(12) United States Patent
Morrell et al.

(10) Patent No.: US 9,963,681 B2
(45) Date of Patent: May 8, 2018

(54) CELLULAR SUBSTRATE FOR NUCLEAR REPROGRAMMING

(75) Inventors: Nicholas Morrell, Cambridge (GB); Mark Ormiston, Cambridge (GB); Amer Rana, Cambridge (GB); Ludovic Vallier, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 198 days.

(21) Appl. No.: 14/008,812

(22) PCT Filed: Mar. 30, 2012

(86) PCT No.: PCT/GB2012/050718
§ 371 (c)(1),
(2), (4) Date: Dec. 6, 2013

(87) PCT Pub. No.: WO2012/131387
PCT Pub. Date: Oct. 4, 2012

(65) Prior Publication Data
US 2014/0093963 A1    Apr. 3, 2014

(30) Foreign Application Priority Data

Mar. 30, 2011   (GB) .................................. 1105413.7

(51) Int. Cl.
*C12N 5/074*      (2010.01)
(52) U.S. Cl.
CPC ...... *C12N 5/0696* (2013.01); *C12N 2501/602* (2013.01); *C12N 2501/603* (2013.01); *C12N 2501/604* (2013.01); *C12N 2501/606* (2013.01); *C12N 2506/28* (2013.01); *C12N 2510/00* (2013.01)

(58) Field of Classification Search
CPC .............. C12N 5/0696; C12N 2510/00; C12N 2501/606; C12N 2501/604; C12N 2501/602; C12N 2501/603; C12N 2506/28
See application file for complete search history.

(56) References Cited

FOREIGN PATENT DOCUMENTS

WO    2011/032166    3/2011

OTHER PUBLICATIONS

Vallier et al., Stem Cells, 27: 2655-2666, 2009.*
Takahashi et al., Cell, 126: 663-676, 2006.*
Stadtfeld. Science, 322: 945-949, 2008.*
Okita. Science, 322: 949-953, 2008.*
Gonzalez. PNAS, 106(22): 8918-8922, 2009.*
Takahashi et al., Cell, 131: 12-12, Nov. 30, 2007.*
Stroncek et al., Tissue Engineering, 15(11): 3473-3486, 2009.*
Nagaoka et al., BMC Developmental Biology, 10:60, 2010.*
Pearson, Jeremy D., "Endothelial progenitor cells—hype or hope?" Journal of Thrombosis and Haemostasis (2009) 7: 255-262.
Pearson, Jeremy D., "Endothelial progenitor cells—an evolving story," Microvascular Research (2010) 79: 162-168.
Pesce, Maurizio et al., "Endothelial and cardiac progenitors: boosting, conditioning and (re)programming for cardiovascular repair," Pharmacology & Therapeutics (2011) 129: 50-61.
Xie XinXing et al., "Another possible cell source for cardiac regenerative medicine: reprogramming adult fibroblasts to cardiomyocytes and endothelial progenitor cells," Medical Hypotheses (2011) 76: 365-367.
International Search Report in PCT/GB2012/050718 dated Jun. 29, 2012.
Staerk et al., "Reprogramming of peripheral blood cells to induced pluripotent stem cells," Cell Stem Cell. Jul. 2, 2010; 7(1): 20-24.
Kim, et al., "Pluripotent stem cells induced from adult neural stem cells by reprogramming with two factors", Nature, vol. 454, pp. 646-651 (2008).
Okita, et al., "Generation of germline-competent induced pluripotent stem cells", Nature, vol. 48, pp. 313-317 (2007).
Park, et al., "Reprogramming of human somatic cells to pluripotency with defined factors", Nature, vol. 451, pp. 141-147 (2008).
Plews, et al., "Activation of Pluripotency Genes in Human Fibroblast Cells by a Novel mRNA Based Approach", PLoS One, 5(12): e14397 (2010). doi:10.1371/journal.pone.0014397.
Warren, et al., "Highly efficient reprogramming to pluripotency and directed differentiation of human cells using synthetic modified mRNA", Cell Stem Cell, 7(5): 618-630 (2010). doi:10.1016/j.stem.2010.08.012.
Yamanaka, "Strategies and New Developments in the Generation of Patient-Specific Pluripotent Stem Cells", Cell Stem Cell, vol. 1, pp. 39-49 (2007).
Yu, et al., "Induced Pluripotent Stem Cell Lines Derived from Human Somatic Cells", Science, vol. 318, pp. 1917-1921 (2007).
Zhou, et al. "Generation of Induced Pluripotent Stem Cells Using Recombinant Proteins", Cell Stem Cell, vol. 4, pp. 381-384 (2009).

* cited by examiner

*Primary Examiner* — Thaian N Ton
(74) *Attorney, Agent, or Firm* — Greenberg Traurig, LLP; Fang Xie

(57) ABSTRACT

This invention relates to the use of late out-growth endothelial progenitor cells (L-EPCs) as a cellular substrate for the generation of Induced pluripotent stem cells (iPSCs). This may be useful in the production of patient-specific tissues for disease modelling, drug and toxicology screening, tissue replacement and delivery of gene therapy.

10 Claims, 8 Drawing Sheets

CELLULAR SUBSTRATE FOR NUCLEAR REPROGRAMMING

CROSS-REFERENCE TO RELATED APPLICATIONS

This application is a National Phase application of International Application No. PCT/GB2012/050718 filed Mar. 30, 2012, which claims priority to GB Application No. GB1105413.7 filed Mar. 30, 2011, the contents of both of which applications are incorporated by reference herein in their entirety.

FIELD OF THE INVENTION

This invention relates to cellular substrates for nuclear reprogramming, for example, for the production of induced pluripotent stem (iPS) cells and other cell types.

BACKGROUND

Nuclear reprogramming of human skin fibroblasts into induced Pluripotent Stem Cells (iPSCs) has revolutionised the field of regenerative medicine (Takahashi K et al Cell 126, 663-676 (2006); Takahashi K., et al. Cell 131, 861-872 (2007)). However, several obstacles prevent the effective translation of iPSC technology for clinical and industrial applications. These include (i) the low kinetics and efficiency with which fibroblasts can be transformed into iPSCs, hindering their high-throughput generation, (ii) the lack of readily accessible cellular substrates, with non-compromised genomes, that can be isolated from patients (Seki T., et al. (2010) Cell Stem Cell 2; 7(1):11-4; Loh Y. H. et al. (2010) Cell Stem Cell. 2; 7(1):15-9; Staerk J., et al., (2010) Cell Stem Cell. 2; 7(1):20-4) (iii) the relative genomic instability of the iPSCs generated and their genomic differences with their somatic progenitors (Hussein, S. M., et al. Nature. 471(7336):58-62 (2011); Martins-Taylor, K. et al (2011). Nat. Biotechnol. 29, 488-91; Yusa et al (2011) Nature 478, 391-4) and (iv) the inability to easily derive feeder-free iPSCs whilst maintaining their pluripotent potential, which is highly desirable for chemically defined differentiation assays, disease modelling, drug testing and development of therapeutics. In addition, it is desirable that the cellular substrate be clonally derived or capable of clonal expansion prior to reprogramming. This allows the generation of a clonal reference genome, which is essential for subsequent high resolution genetic testing such as array Comparative Genome Hybridisation (aCGH) and genome sequencing comparisons Several improvements in the efficiency of iPSC generation have been reported since their inception, including the use of progenitor/stem cells as cellular substrates and the inclusion of chemical enhancers in reprogramming protocols, although not all have been demonstrated to work in human samples (Feng B., et al. Cell Stem Cell. 4(4):301-12 (2009)). While compounds such as methylation and deacetylation inhibitors, modified mRNA, siRNAs and vitamin C have been shown to increase the reprogramming efficiency of skin fibroblasts to varying degrees, and may prove useful in translational applications, it would be desirable to manipulate the cellular substrate for reprogramming as little as possible. Moreover, skin cells may carry mutations due to their higher exposure to external environmental conditions (Seki et al 2010; Loh et al 2010; Staerk et al 2010). In addition, for some patients, such as those on anticoagulants or those with conditions that affect wound healing (Shore E. M., et al. Nat. Genet. 38 (5): 525-7 (2006)), skin biopsies are neither practical nor desirable.

Haematopoietic stem cells derived from the bone marrow compartment have been shown to reprogram with higher efficiency than skin fibroblasts in the absence of chemical enhancers, presumably due to a more permissive epigenetic state (Okabe M., et al. Blood. 27; 114(9):1764-7 (2009); 5. Eminli S., et al. Nat. Genet. 41 (9):968-76. (2009)). However obtaining these cells routinely from patients is not trivial, requiring invasive bone marrow aspiration or blood mobilization.

The reprogramming of T-cells and myeloid cells from peripheral blood has also been demonstrated (Seki et al 2010; Loh et al 2010; Staerk et al 2010). These investigators have shown it is possible to circumvent the need for invasive procedures to generate patient specific iPSCs, as blood sampling is routine for almost all patients. However the use of these cells presents at least two major problems: (i) circulating T-cells will possess permanent rearrangements of their genomes following T-cell receptor gene recombination events, thus limiting the potential uses of the iPSC derived from them and (ii) the generation of iPSCs from blood obtained from patients with blood cell related diseases could prove difficult. For example, myeloid derived iPSCs from patients with leukaemia carrying the Philadelphia chromosome rearrangement would not be useful for developing personalised cellular therapies.

Recently, the epigenomic and genomic stability of iPSCs has been called into question (Hussein, S. M., et al. Nature. 471(7336):58-62 (2011); Gore, A., et al. Nature. 471(7336): 63-7 (2011); Lister, R., et al. Nature. 471(7336):68-73 (2011)). A variety of iPSCs generated from either fibroblasts or adipose-derived stem cells, via either viral integration or non-integrative methods including episomal or mRNA based expression of the reprogramming factors, were compared at the methylome, chromosome, and exome levels to the parent lines used to generate them, along with hESCs. In summary, all the iPSC lines regardless of the parental cell type or the method used showed independent differences to their parental line, with each other and to hESCs, which were in a relative ground state of pluripotency. This is a major concern that will need to be addressed if iPSCs are to be used in cellular therapies, although with sufficient controls (e.g. repeatability across lines) this need not preclude them from development as models of specific diseases and in drug/toxicology screens, which is an especially important consideration for the pharmaceutical industry.

BRIEF SUMMARY OF THE INVENTION

The present inventors have identified a reprogramming substrate which offers significant benefits over fibroblasts, T cells and other substrates previously used for reprogramming. Although they can be readily obtained from blood samples, late out-growth endothelial progenitor cells (L-EPCs) are free from major rearrangements or acquired mutations and are shown herein to be reprogrammed with high efficiency with minimal cellular and chemical manipulation. Late out-growth endothelial progenitor cells may therefore be useful, for example, in high-throughput and standardised nuclear reprogramming techniques for the development of cellular and drug therapies.

An aspect of the invention provides a method of producing reprogrammed mammalian cells comprising (i) providing one or more late-outgrowth endothelial progenitor cells (L-EPCs), and
(ii) reprogramming said late-outgrowth endothelial progenitor cells into reprogrammed cells.

Another aspect of the invention provides the use of late-outgrowth EP cells (L-EPCs) as a substrate for nuclear reprogramming.

Another aspect of the invention provides the use of late outgrowth EP cells as a substrate for the production of reprogrammed (directly differentiated) cells.

DETAILED DESCRIPTION OF THE INVENTION

Figure 1A:
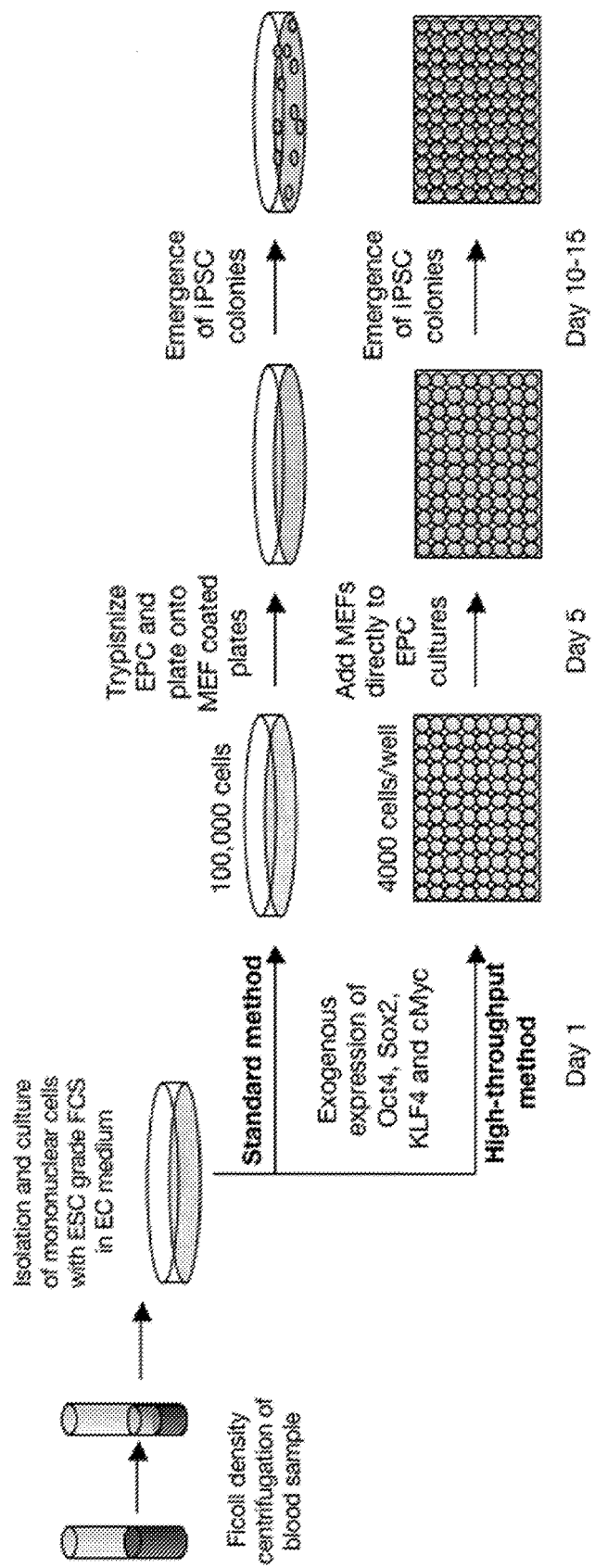
FIGS. 1A-1C show a summary of methodology and basic characterization of EPC-iPSCs.

Reprogrammed cells may include mammalian cells, for example pluripotent cells, such as iPS cells, or differentiated or partially differentiated cells of any cell type, including cells of ectodermal, endodermal, extra-embryonic ectodermal and mesodermal lineages. For example, reprogrammed cells may include cardiovascular cells, such as cardiomyocytes.

Late outgrowth EP cells (also known as blood outgrowth endothelial cells) are highly proliferative blood-derived endothelial-like cells that arise from the mononuclear cell fraction of peripheral blood under endothelial-selective conditions and are able to spontaneously form tubular structures in culture and contribute to new vessel formation when delivered in vivo (Pitchford S. C., et al. *Cell Stem Cell.* 9; 4(1):62-72 (2009); Yoder, M., et al. *Blood* 109(5):1801-9 (2007); Piaggio, G., et al. *Blood* 114(14):3127-30 (2009); Hur et al Arterioscler Thromb Vasc Biol. 2004 February; 24(2):288-93). Late-outgrowth EP cells are free from major genomic rearrangements or acquired hematopoietic mutations Although late-outgrowth EP cells resemble endothelial cells in many molecular and cellular characteristics, they display increased proliferation compared to endothelial cells and express different markers.

Late-outgrowth EP cells express VEGFR2 (vascular endothelial growth factor 2), CD31 (cluster of differentiation 31) and CD34 and do not express the leukocyte and monocyte markers CD45 and CD1.

Preferably, late-outgrowth EP cells in culture have the phenotype CD31high: CD34+: CD146+: KDR+: vWF+: CD14−: CD45−.

Cell surface markers expressed by a cell may be readily identified using standard techniques, such as flow cytometry, PCR, western blotting, immunocytochemistry and in situ hybridisation.

Late-outgrowth endothelial progenitor (EP) cells may be produced from a sample of blood, preferably venous blood, obtained from an individual, at any stage of development or age. Suitable techniques are known in the art (Lin, Y., et al. *J Clin Invest.* 105(1):71-7 (2000); Medina et al. (2010) Invest. Ophthalmol. Vis. Sci. 51, 5906-13) and described herein. A method described herein may include the step of obtaining a sample of blood from an individual. Methods for obtaining blood samples from individuals are routine in the art. For example, L-EPCs may be isolated from the mononuclear cell fraction of peripheral venous blood by plating for 10 to 14 days on collagen and isolating colonies of proliferating L-EPCs from other cell types, which are either senescent or non-dividing.

In some embodiments, the mononuclear cell fraction may be frozen and thawed before isolation of L-EPCs.

The individual may be a mammal, preferably a human.

In some embodiments, the individual may be healthy (i.e. without any disease condition).

In other embodiments, the individual may have a disease condition.

Late-outgrowth EP cells may be produced from individuals with any disease condition. Suitable disease conditions include conditions associated with diseased, damaged or dysfunctional cells or tissue within the body of the individual. For example, the individual may have diseased, damaged or dysfunctional cells or tissue selected from epithelial, cardiac, smooth muscle, neural, hepatic, renal, haemopoetic, endothelial, skeletal muscle, bone, lung, gastrointestinal, pancreatic, connective and reproductive cells or tissue.

For example, an individual may have a disease condition selected from genetic diseases, metabolic diseases, cancer, blood disorders, cardiovascular disorders and diseases associated with aberrant TGFβ superfamily signalling.

Genetic diseases may include any single gene disorders such as familial hypercholesterolemia, polycystic kidney disease, hereditary spherocytosis, Marfan syndrome, Huntington's disease, sickle cell anaemia, cystic fibrosis, Tay-Sachs disease, beta-thalassemias, alpha-thalassemias, phenylketonuria, hereditary hemochromatosis, glycogen storage diseases, galactosemia, duchenne muscular dystrophy, and hemophilia.

Metabolic diseases may include glycogen storage disorders, defects in fructose, galactose and glycerol metabolism, such as hyperglycerolemia, defects in cholesterol and lipoprotein metabolism, such as hyperlipidemia and hyperlipoproteinemia, mucopolysaccaridoses, disorders of glycosphingolipid metabolism, such as gangliosidoses, oligosaccharidoses, such as fucosidosis, defects in amino acid and organic acid metabolism, such as phenylketonuria and tyrosinemia.

Cancers may include any type of solid cancer or malignant lymphoma and especially leukaemia, sarcomas, skin cancer, bladder cancer, breast cancer, uterus cancer, ovary cancer, prostate cancer, lung cancer, colorectal cancer, cervical cancer, liver cancer, head and neck cancer, oesophageal cancer, pancreas cancer, renal cancer, stomach cancer and cerebral cancer. Cancers may be familial or sporadic.

Blood disorders may include haemophilia and polycythemia vera.

Cardiovascular disorders may include atherosclerosis, ischaemic (coronary) heart disease, myocardial ischaemia (angina), myocardial infarction, aneurismal disease, atheromatous peripheral vascular disease, aortoiliac disease, chronic and critical lower limb ischaemia, visceral ischaemia, renal artery disease, cerebrovascular disease, stroke, atherosclerotic retinopathy, thrombosis and aberrant blood clotting, and hypertension, including pulmonary arterial hypertension.

In some embodiments, late-outgrowth EP cells obtained from an individual with a disease condition may display a disease phenotype, for example late-outgrowth EP cells from an individual with pulmonary arterial hypertension associated with a somatic bmpr2 mutation may display the disease phenotype (Toshner et al, AJRCCM (2009) 180(8): 780-7).

In other embodiments, late-outgrowth EP cells obtained from an individual with a disease condition may display a normal phenotype. For example late-outgrowth EP cells from an individual with a hematopoietic condition such as polycythemia vera or CML associated with the Philadelphia chromosome, may lack any disease associated mutation. Late-outgrowth EP cells may be produced by a method which comprises:
  (i) isolating the mononuclear cell fraction from a blood sample, and,
  (ii) culturing the fraction in endothelial cell culture medium for at least 8 days.

The mononuclear cell fraction may be isolated from a blood sample by any suitable technique. For example, the sample may be separated by density gradient centrifugation and the mononuclear cell layer extracted from the gradient using standard techniques.

Suitable endothelial cell culture media for culturing the mononuclear cell fraction may comprise a basal medium optimized for the growth of human endothelial cells in the absence of bovine brain extract. The medium may comprise additional growth factors, including VEGF (vascular endothelial growth factor), IGF (Insulin-like growth factor), EGF (epidermal growth factor) and bFGF (basic fibroblast growth factor), as well as ascorbic acid and hydrocortisone. In some embodiments, endothelial cell culture media may lack heparin. Suitable endothelial cell culture media are well-known in the art and include Endothelial Cell Growth Medium-MV2 (Promo-cell), Microvascular Endothelial Cell Growth Medium-2 (EGM™-2MV; Lonza AG) and M199 medium plus VEGF and/or FGF. Preferably, the mononuclear cell fraction is cultured on a collagen coated surface, such as a tissue culture vessel.

Methods for culturing mammalian cells are well-known in the art (see, for example, Basic Cell Culture Protocols, C. Helgason, Humana Press Inc. U.S. (15 Oct. 2004) ISBN: 1588295451; Human Cell Culture Protocols (Methods in Molecular Medicine S.) Humana Press Inc., U.S. (9 Dec. 2004) ISBN: 1588292223; Culture of Animal Cells: A Manual of Basic Technique, R. Freshney, John Wiley & Sons Inc (2 Aug. 2005) ISBN: 0471453293, Ho W Y et al J Immunol Methods. (2006) 310:40-52, Handbook of Stem Cells (ed. R. Lanza) ISBN: 0124366430). Media and ingredients thereof may be obtained from commercial sources (e.g. Gibco, Roche, Sigma, Europa bioproducts, R&D Systems). Standard mammalian cell culture conditions may be employed, for example 37° C., 21% Oxygen, 5% Carbon Dioxide. Culture medium is preferably changed every two days and cells allowed to settle by gravity.

Late-outgrowth EP cells in the mononuclear cell fraction are highly proliferative, whereas other cells in the fraction (i.e. early-outgrowth EP cells) are non-proliferative and eventually die off during culture. Regular passaging of the mononuclear cell fraction therefore results in a pure culture of late-outgrowth EP cells.

The mononuclear cell fraction may be cultured in the endothelial cell culture medium until only late-outgrowth EP cells remain in the culture (i.e. all or substantially all the cells in the culture are late-outgrowth EP cells).

For example, the mononuclear cells may be cultured in the endothelial cell culture medium for at least 8, 9, 10, 11, 12, 13, 14 or 15 days. Typically, cells are cultured for 8 to 21 days.

Once a pure culture has been achieved, the late-outgrowth EP cells may be passaged and expanded as required in the endothelial cell culture medium using standard cell culture techniques.

In some embodiments, a method may comprise identifying or confirming the identity of late-outgrowth EP cells in the culture.

Late-outgrowth EP cells may be identified from their growth rate or morphology. For example, late-outgrowth EP cells may display a cobble stone morphology which is characteristic of endothelial-type cells. Late-outgrowth EP cells may also be identified by determining the presence of cellular markers, such as VEGFR2 and/or CD34. For example, a conventional flow assay may be employed.

Following the production of late outgrowth EP cells, the cells may be reprogrammed.

Late outgrowth EP cells may be reprogrammed by introducing reprogramming factors into the cells.

Reprogramming factors may be introduced in the form of nucleic acids (Warren L et al. *Cell Stem Cell*. 2010 Nov. 5; 7(5):618-30) or proteins (Zhou H, et al Cell Stem Cell. 2009 May 8; 4(5):381-4) by any suitable technique, including plasmid or more preferably, viral transfection, direct protein delivery or direct delivery of nucleic acid, such as mRNA. Following introduction of the reprogramming nucleic acids or proteins, the population of treated cells may be cultured. For example, late outgrowth EP cells may reprogrammed by;
  (i) expressing nucleic acid encoding one or more reprogramming factors in the late outgrowth EP cells, or;
  (ii) contacting the late outgrowth EP cells with one or more reprogramming factor mRNAs or one or more reprogramming factor proteins.

The one or more reprogramming factors which are employed depend on the type of reprogrammed cell which is desired.

For example, cardiomyocytes may be produced by introducing reprogramming factors Gata4, Mef2c, and Tbx5 into late-outgrowth EP cells (Vierbuchen T et al Nature. 2010 Feb. 25; 463(7284):1035-41). Muscle cells may be produced by introducing reprogramming factor MyoD into late-outgrowth EP cells (Zhou H, et al Cell Stem Cell. 2009 May 8; 4(5):381-4). Neural cells may be produced by introducing reprogramming factors Ascl1, Brn2 (also called Pou3f2) and Myt1l into late-outgrowth EP cells (Vierbuchen et al (2010)). Suitable reprogramming factors for producing other types of reprogrammed cells are well-known in the art.

In some embodiments, nucleic acid encoding one or more reprogramming factors may be expressed in one or more late outgrowth EP cells. For example, the nucleic acid may be operably linked to inducible or non-inducible regulatory elements within a suitable vector, for example a retroviral vector, for expression within the cells. Vectors containing the nucleic acid are then transfected into the late outgrowth EP cells. Any convenient technique for the transfection may be employed. Following transfection, the one or more reprogramming factors are expressed in the late-outgrowth EP cells and reprogram it. In other embodiments, transposon-mediated or other random integration transgenesis techniques may be employed. Reprogramming cells though expression of nucleic acid encoding one or more reprogramming factors is well-known in the art (Takahashi et al 2007; Takahashi et al 2007; Seki et al 2010; Loh et al 2010; Staerk et al 2010).

In some preferred embodiments, late-outgrowth EP cells may be reprogrammed with minimal or no genetic modification to the cells. Suitable techniques are known in the art and include the use of excisable lentiviral and transposon vectors; repeated application of transient plasmid, episomal and adenovirus vectors or; the use of small molecules, synthetic mRNA and/or microRNAs (Sidhu K S. Expert Opin Biol Ther. (2011) May; 11(5):569-79; Woltjen K et al (2009) Nature 458 (7239):766-70; Chou B K et al. Cell Res. 2011 21(3):518-29).

In other embodiments, one or more reprogramming factor proteins or reprogramming factor nucleic acids, such as mRNA, may be contacted with a late outgrowth EP cell. The reprogramming factor proteins or nucleic acids are then introduced into the late outgrowth EP cell. Reprogramming cells though contact with reprogramming factor nucleic acids (Warren L et al. *Cell Stem Cell*. 2010 Nov. 5; 7(5): 618-30) or proteins (Zhou H, et al Cell Stem Cell. 2009 May 8; 4(5):381-4) is well known in the art and any suitable technique may be employed. For example, reprogramming factor proteins or nucleic acid may be cultured in the presence of the late outgrowth EP cell under conditions which allow for entry of the proteins or nucleic acid into the cell. In some embodiments, entry of reprogramming factor proteins into the cell may be facilitated by a membrane penetrating peptide, which may be linked or attached to the reprogramming factor proteins. Reprogramming factor proteins or reprogramming factor nucleic acid may be introduced into late outgrowth EP cells by traditional methods such as lipofection, electroporation, calcium phosphate precipitation, particle bombardment and/or microinjection, or may be delivered into cells by a protein delivery agent. For example, the reprogramming factor proteins or reprogramming factor nucleic acid can be introduced into cells by covalently or noncovalently attached lipids, e.g. a myristoyl group.

Reprogramming factor nucleic acids for direct delivery into late outgrowth EP cells may be translatable by endogenous translation factors within the cell. A suitable synthetic mRNA may be modified. For example, 5-methylcytidine may be substituted for cytidine, and pseudouridine for uridine, followed by phosphatase treatment (Zhou H, et al 2009).

Following the introduction of reprogramming factors into the late-outgrowth EP cells, the cells may be culture in endothelial cell culture medium, for example EGM-2MV supplemented with 10% fetal bovine serum (FBS), for 1 or more, 2 or more, 3 or more, 4 or more, or 5 or more days, preferably about 5 days.

Following culture in endothelial cell culture medium, the cells may then be cultured in a suitable reprogrammed cell medium, optionally on feeder cells. Suitable media are well known in the art. For example, iPS cells may be cultured in KSR (knockout serum replacement) supplemented with $FGF_2$.

In some preferred embodiments, late outgrowth EP cells may be reprogrammed in a chemically defined medium (CDM) without feeder cells.

A CDM is a nutritive solution for culturing cells which contains only specified components, preferably components of known chemical structure. A CDM is devoid of components which are not fully defined, such as such as Foetal Bovine Serum (FBS), Bovine Serum Albumin (BSA), and feeder cells. In some embodiments, a CDM may be humanised and may be devoid of components from non-human animals. Suitable CDMs are well known in the art and described in more detail below.

Media and ingredients thereof may be obtained from commercial sources (e.g. Gibco, Roche, Sigma, Europabio-products). In a humanised CDM, for example BSA may be replaced in CDM by Polyvinyl alcohol (PVA), human serum albumin, Plasmanate™ (human albumin, alpha-globulin and beta globulin: Talecris Biotherapeutics NC USA) or Buminate™ (human albumin: Baxter Healthcare), all of which are available from commercial sources.

In some embodiments, late-outgrowth EP cells may be reprogrammed into differentiated cells using the methods described herein. For example, the reprogrammed cells may be epithelial, cardiac, smooth muscle, neural, hepatic, renal, haemopoetic, endothelial, skeletal muscle, bone, lung, gastrointestinal, pancreatic, connective tissue or reproductive cells. Cardiac cells may include cardiac muscle cells, such as cardiomyocytes (Ieda et al Cell 2010 142 375-386).

Late outgrowth EP cells may be reprogrammed into cardiomyocytes by introducing the reprogramming factors Gata4, Mef2c, and Tbx5 into the cells. For example a method may comprise;
 (i) expressing nucleic acid encoding Gata4, Mef2c, and Tbx5 in the late outgrowth EP cells, or,
 (ii) contacting the late outgrowth EP cells with Gata4, Mef2c, and Tbx5 nucleic acid or proteins.

The amino acid sequences of Gata4, Mef2c, and Tbx5 are readily available on public databases. For example the amino acid sequence of Mef2C (Gene No: 4208) has the NCBI database entry NP_001180279.1 GI: 301069386; the amino acid sequence of Gata4 (Gene No:2626) has the NCBI database entry NP_002043.2 GI:33188461 and the amino acid sequence of Tbx5 (Gene No:6910) has the NCBI database entry NP_000183.2 GI:1820189.

Following introduction of the reprogramming factors, cells may be cultured in an endothelial cell culture medium for at least 2 days. The cells may then be cultured in a suitable cardiomyocyte culture medium.

Following reprogramming, cardiomyocytes may be isolated, cultured and/or expanded.

Cardiomyocytes produced as described herein may be useful in repairing damaged or dysfunctional cardiac tissue; screening for compounds using in the treatment of damaged or dysfunctional cardiac tissue; disease modelling and toxicology screens.

Late outgrowth EP cells may be reprogrammed into muscle cells by introducing the reprogramming factors MyoD into the cells. For example a method may comprise;
 (i) expressing nucleic acid encoding MyoD in the late outgrowth EP cells, or,
 (ii) contacting the late outgrowth EP cells with MyoD nucleic acid or protein.

The amino acid sequence of MyoD is readily available on public databases. For example the amino acid sequence of human MyoD (Gene No: 4654) has the NCBI database entry NP_002469.2 GI: 23111009.

Following introduction of the reprogramming factors, cells may be cultured in an endothelial cell culture medium for at least 2 days. The cells may then be cultured in a suitable muscle cell culture medium.

Following reprogramming, muscle cells may be isolated, cultured and/or expanded.

Muscle cells produced as described herein may be useful in repairing damaged or dysfunctional muscle tissue; screening for compounds using in the treatment of damaged or dysfunctional muscle tissue; disease modelling and toxicology screens.

Late outgrowth EP cells may be reprogrammed into neural cells by introducing the reprogramming factors Ascl1, Brn2 (also called Pou3f2) and Myt1 into the cells. For example a method may comprise;

(i) expressing nucleic acid encoding Ascl1, Brn2, and Myt1 into the late outgrowth EP cells, or, (ii) contacting the late outgrowth EP cells with Ascl1, Brn2 and Myt1 nucleic acid or proteins.

The amino acid sequences of Ascl1, Brn2, and Myt1 are readily available on public databases. For example the amino acid sequence of human Ascl1 (Gene No: 429) has the NCBI database entry NP_004307.2 GI: 55743094; the amino acid sequence of Brn2 (Gene No: 5454) has the NCBI database entry NP_005595.2 GI: 51702521; and the amino acid sequence of Myt1 (Gene No: 4661) has the NCBI database entry NP_004526.1 GI: 17975763.

Following introduction of the reprogramming factors, cells may be cultured in an endothelial cell culture medium for at least 2 days. The cells may then be cultured in a suitable neural culture medium.

Following reprogramming, neural cells may be isolated, cultured and/or expanded.

Neural cells produced as described herein may be useful in repairing damaged or dysfunctional neural tissue; screening for compounds using in the treatment of damaged or dysfunctional neural tissue; disease modelling and toxicology screens.

In other embodiments, late outgrowth EP cells may be reprogrammed into pluripotent cells, such as iPS cells.

A pluripotent mammalian cell is an unspecialized cell that is capable of replicating or self-renewing itself and developing into specialized cells of all three primary germ layers i.e. ectoderm, mesoderm and endoderm but are not able to develop into all embryonic and extra-embryonic tissues (i.e. not totipotent).

iPS cells are pluripotent cells which are derived from non-pluripotent ancestor cells. Ancestor cells are typically reprogrammed into iPS cells through the introduction of reprogramming factors, such as Oct4, Sox2, Klf4 and c-Myc into the cell. Reprogramming factors and techniques for the production of iPS cells are well-known in the art (Yamanaka et al Nature 2007; 448:313-7; Yamanaka 6 2007 June 7; 1(1):39-49. Kim et al. Nature. 2008 Jul. 31; 454(7204):646-50; Takahashi Cell. 2007 Nov. 30; 131(5):861-72. Park et al Nature. 2008 Jan. 10; 451(7175):141-6; Kimet al Cell Stem Cell. 2009 Jun. 5; 4(6):472-6; Vallier, L., et al. (2009) Stem Cells 27, 2655-66.). iPS cells express the pluripotency associated markers Oct4, Sox2, alkaline phosphatase and Nanog.

For reprogamming into iPS cells, late outgrowth EP cells may treated with Oct4, Sox2, Klf4 and c-Myc in accordance with standard techniques, by introducing Oct4, Sox2, Klf4 and c-Myc into the cells, for example by plasmid or more preferably, viral transfection, direct protein delivery or direct delivery of nucleic acid, such as mRNA. For example, late outgrowth EP cells may be reprogrammed into iPS cells by;

(i) expressing nucleic acid encoding Oct4, Sox2, Klf4 and c-Myc in the cells, or (ii) introducing Oct4, Sox2, Klf4 and c-Myc mRNA, or protein into the cells.

The amino acid sequences of Oct4, Sox2, Klf4 and c-Myc are readily available on public databases. For example the amino acid sequence of human Oct4 (Pou5F1: Gene No: 5460) has the NCBI database entry NP_002692.2 GI:42560248; the amino acid sequence of human Sox2 (Gene No:6657) has the NCBI database entry NP_003097.1 GI:28195386; the amino acid sequence of human Klf4 (Gene No:9314) has the NCBI database entry NP_004226.3 GI:194248077; and the amino acid sequence of human c-Myc (Gene No:4609) has the NCBI database entry NP_002458.2 GI:71774083.

In some embodiments, late-outgrowth EP cells may also be treated with one or more additional reprogramming factors, such as Nanog, ESRRB, Lin28, NR5A2, DNMT3β, REX1 and SALL4 (see for example, Plews J R et al PLoS One. 2010 Dec. 30; 5(12):e14397).

Other suitable reprogramming factors and combinations of reprogramming factors for inducing pluripotency are known in the art. (see, for example, Yu et al Science 318 2007 1917-1920, Tesar, P. J. et al. Nature 448, 196-199 (2007); Nichols, J. & Smith, A. Cell Stem Cell 4, 487-492 (2009); Ying, Q. L. et al. Nature 453, 519-523 (2008), Hanna J, et al Proc Natl Acad Sci U S A. 2010 May 18; 107(20): 9222-7; Han D W, et al Nat Cell Biol. 2011 January; 13(1):66-71; Silva J et al Cell. 2009 Aug. 21; 138(4):722-37).

In some embodiments, reprogramming promoting agents, such as methylation and deacetylation inhibitors, modified mRNA, siRNAs, such as P53 siRNA, valproic acid, BIX01294, 5'-aza-2'-deoxycytidine and vitamin C, may also be used to increase reprogramming efficiency further, if required (see for example Flews J R et al PLoS One. 2010 Dec. 30; 5(12):e14397 and references cited therein).

In other embodiments, late outgrowth EP cells may be reprogrammed in the absence of reprogramming promoting agents.

Following introduction of the reprogramming factors, the cells may be cultured in cell culture medium and optionally, screened for expression of reprogramming factors using standard techniques.

As described above, cells may be cultured in endothelial cell culture medium for at least one day after treatment with reprogramming factors. For example, the cells may be cultured in endothelial cell culture medium for 1, 2, 3, 4 or 5 or more days. The cells may then be cultured an appropriate medium for the reprogrammed cells. For example, iPS cells may be cultured in KSR supplemented with fgf2, in the presence of feeder cells.

Suitable cell culture conditions are well known in the art (Vallier, L. et al Dev. Biol. 275, 403-421 (2004), Cowan, C. A. et al. N. Engl. J. Med. 350, 1353-1356 (2004), Joannides, A. et al. Stem Cells 24, 230-235 (2006) Klimanskaya, I. et al. Lancet 365, 1636-1641 (2005), Ludwig, T. E. et al. Nat. Biotechnol. 24, 185-187 (2006)).

In some preferred embodiments, the treated cells may be cultured in a CDM. Suitable CDMs may include CDM-PVA plus 10 ng/ml fgf2 and activin 10 ng/ml for feeder free CDM cultures.

Suitable CDMs include Knockout (KS) medium supplemented with 4 ng/ml FGF$_2$; Knockout Dulbecco's Modified Eagle's Medium (KO-DMEM) supplemented with 20% Serum Replacement, 1% Non-Essential Amino Acids, 1 mM L-Glutamine, 0.1 mM β-mercaptoethanol and 4 ng/ml to 10 ng/ml human FGF2; and DMEM/F12 supplemented with 20% knockout serum replacement (KSR), 6 ng/ml FGF2 (PeproTech), 1 mM L-Gln, 100 μm non-essential amino acids, 100 μM 2-mercaptoethanol, 50 U/ml penicillin and 50 mg/ml streptomycin and TeSR (Ludwig et al Nat Biotech 2006 24 185). Other suitable CDM which may be used in accordance with the present methods are known in the art (e.g. N12 medium, Johansson and Wiles CDM; Johansson and Wiles (1995) Mol Cell Biol 15, 141-151).

Suitable humanised CDMs may comprise a basal culture medium, such as IMDM and/or F12 supplemented with insulin, for example at 0.5 μg/ml to 70 μg/ml, transferin, for example at a concentration of 1.5 μg/ml to 150 μg/ml, an antioxidant, such as 1-thiolglycerol, for example at a concentration of 45 μM to 4.5 mM, lipids, and one or more of human serum albumin, polyvinyl alcohol (PVA), Plasmanate™ (human albumin, alpha-globulin and beta globulin: Talecris Biotherapeutics NC USA) or Buminate™ (human albumin: Baxter Healthcare), for example at a concentration of 0.5 mg/ml to 50 mg/ml. For example, humanised CDM include humanised Johansson and Wiles CDM, which consists of: 50% IMDM (Gibco) plus 50% F12 NUT-MIX (Gibco); 7 µg/ml insulin; 15 µg/ml transferrin; 5 mg/ml human serum albumin, polyvinyl alcohol (PVA), Plasmanate™ or Buminate™; 1% chemically defined lipid concentrate (Invitrogen); and 450 µM 1-thiolglycerol.

Following treatment of the late out-growth EP cells with reprogramming factors, reprogrammed cells, such as iPS cells, may be identified in the cell culture after at least 6, 7, 8, 9 or 10 days.

As shown herein, late outgrowth EP cells are more amenable than fibroblasts to reprogramming and reprogrammed cells produced from late outgrowth EP cells may appear before corresponding reprogrammed cells produced from fibroblasts under identical conditions. For example, late outgrowth EP cell derived iPS cells may be identifiable at least 1, 2, 3, 4, or 5 days before corresponding fibroblast derived iPS cells.

Late outgrowth EP cells may also be reprogrammed more efficiently than fibroblasts under identical conditions. For example, under identical conditions, a population of late outgrowth EP cells may produce at least 2 fold, at least 5 fold or at least 10 fold more reprogrammed cells than an identical population of fibroblasts.

Reprogrammed cells produced from late outgrowth EP cells may also display increased proliferation relative to be corresponding reprogrammed cells produced from fibroblasts under identical conditions. This high proliferation facilitates isolation and expansion of the reprogrammed cells. The amount of proliferation of reprogrammed cells may be determined by any convenient technique, for example, cell counting, BrdU staining and/or flow cytometry.

In some embodiments, the reprogrammed cells are iPS cells. iPS cells produced from late outgrowth EP cells are shown herein to be (i) karyotypically normal (ii) Nanog and alkaline phosphatase positive, (iii) display demethylation of the Oct4 promoter, are, and have (iv) exogenous expression of the reprogramming factors silenced. iPS cells produced from late outgrowth EP cells may be less prone to autonomous differentiation (i.e. display increased stability) relative to fibroblast derived iPS cells. Autonomous differentiation may be determined by standard techniques such as cellular morphology or flow cytometry.

In some embodiments, cells reprogrammed from a population of late outgrowth EP cells may be identified or characterised.

For example, the presence or absence of cell markers may be monitored or detected.

In some embodiments, cells may be tested for presence of cell markers associated with the reprogrammed cell type. Cells which express the markers may be identified as reprogrammed cells. For example, iPS cells may identified by expression of one or more of Oct4, Sox2, alkaline phosphatase, Tra-1-60 and Nanog.

In other embodiments, cells may be tested for absence of cell markers associated with late outgrowth EP cells, such as CD34 and CD31, and/or the continued absence of leukocyte lineage markers, such as CD1 and CD45. Cells which lack late outgrowth EP cell markers may be identified as reprogrammed cells.

A method may further comprise isolating and/or purifying the reprogrammed cells. Cells may be separated from other cell types in the population using any technique known to those skilled in the art, including those based on the recognition of extracellular epitopes by antibodies and/or magnetic beads or fluorescence activated cell sorting (FACS), including the use of antibodies against extracellular regions of characteristic markers.

Populations of reprogrammed cells produced from late outgrowth EP cells as described herein may contain fewer copy number variations (CNVs) than populations of reprogrammed cells produced from fibroblasts or other known reprogramming substrates.

Reprogrammed cells may be cultured and/or expanded to generate a homogenous or substantially homogenous population of reprogrammed cells. Suitable techniques for mammalian cell culture are well known in the art and described elsewhere herein.

In some embodiments, the reprogrammed cells may be iPS cells. iPS cells produced as described herein may be allowed to differentiate into partially or fully differentiated cell types. For example, iPS cells produced as described herein may be differentiated into epithelial, cardiac, smooth muscle, neural, hepatic, renal, haemopoetic, endothelial, skeletal muscle, bone, lung, gastrointestinal, pancreatic, connective tissue and reproductive tissue cells. Suitable techniques for the differentiation of iPS cells are well known in the art (see for example, Okita K. Curr Opin Organ Transplant. 2010 Dec. 9 and references cited therein).

Reprogrammed cells may be used for screening.

Screening may include drug or small molecule screening. For example, the isolated reprogrammed cells may be contacted with a test compound and the effect of the test compound on the cells is determined. Screening may also include functional genomic screening. For example, a gene may be suppressed, knocked out or otherwise inactivated in the isolated reprogrammed cells and the effect of the inactivation on the cells determined.

In some embodiments, iPS cells may be produced from late outgrowth EP cells as described herein. The late outgrowth EP cells may be from a normal individual or an individual with a disease condition. After reprogramming, the iPS cells may be differentiated into a cell type which is affected in the disease condition. The differentiated cells may express a detectable reporter or display an observable cellular phenotype which differs between disease affected cells and normal cells. The differentiated cells may be exposed to test compounds and the effect of the test compound on the reporter expression or observable cellular phenotype determined. Compounds which cause the cells to revert from disease cell state to the normal state may be identified. Alternatively, the one or more genes in the differentiated cells may be inactivated, for example by targeted mutation or RNAi suppression, and the effect of the inactivation on the reporter expression or observable cellular phenotype determined. Genes whose inactivation causes the cells to revert from disease cell state to the normal state may be identified.

Screening may include toxicology screening. For example, the isolated reprogrammed cells may be contacted with a test compound at various concentrations that mimic abnormal/normal concentrations in vivo. The effect of the test compound on the cells may be determined and toxic effects identified. Toxicology screening is well known in the art (see for example Barbaric I et al. Biochem Soc Trans. 2010 August; 38(4):1046-50).

Reprogrammed cells (and cells derived from reprogrammed cells, such as differentiated cells) may also be used for the treatment of an individual, for example for the repair or replacement of damaged or diseased tissue in an individual. Reprogrammed cells may be useful for the replacement, enhancement and/or stimulation of tissue in an individual. Tissue replacement involves the replacement of dead or dysfunctional cells in an individual by transplanting appropriately differentiated iPSCs to region of cell death. Examples include the transplant of new cardiomyocytes to an ischemic heart, and the transplant of new hepatocytes to a damaged liver. Tissue enhancement involves transplanting cells to add extra tissue bulk when tissue loss has occurred in an individual, for example in bone or skeletal muscle. Tissue stimulation involves stimulating the body to repair itself or enhance the immune system or other endogenous repair mechanisms.

The individual may be the same individual from whom the original blood sample was obtained.

In some embodiments, the reprogrammed cells may, for example, be admixed with a pharmaceutical acceptable carrier in a pharmaceutical composition. The composition may be administered to the individual.

Reprogrammed cells may also be used for drug delivery, targeted tissue ablations and other gene therapy strategies which require a cellular vector. For example, reprogrammed cells may be made transgenic to express proteins or other molecules which are deficient in an individual, or to release proteins or other molecules that will kill surrounding cells. These delivery cells (cellular vectors) may be maintained at appropriate levels following administration to the individual or may be ablated by the presence of suicide genes or by administration or withdrawal of an exogenous drug.

Reprogrammed cells may also be used for disease modelling. For example, cells may be reprogrammed into a cell type affected in a disease condition, either directly or by producing iPS cells which are then differentiated into the affected cell type. The effect of the mutation on the cellular phenotype may be studied and the genetic and/or biochemical interactors that contribute to the cellular pathology of the disease may be identified and/or characterised.

The efficiency of reprogramming of late-outgrowth EP cells makes them suitable for high through-put applications.

For example, cells from two or more, five or more, ten or more, twenty or more, thirty or more, forty or more, or fifty or more independent late-outgrowth EP cell lines may be reprogrammed simultaneously. The independent late-outgrowth EP cell lines may be derived from the same or different individuals. For example, late-outgrowth EP cells from cell lines derived from two or more, five or more, ten or more, twenty or more, thirty or more, forty or more, or fifty or more different individuals may be reprogrammed simultaneously.

Conveniently, late-out-growth EP cells from cell-lines derived from up to 48 individuals may be reprogrammed simultaneously on a single 96 well tissue culture dish. Of course, multiple dishes of cells may be reprogrammed simultaneously under the same conditions to reprogram, cells derived from more than 48 individuals.

For example, a method of producing reprogrammed mammalian cells may comprise;
(i) providing samples of blood obtained from a population individuals,
(i) producing a population of late-outgrowth EP cells from each of said samples,
(ii) simultaneously reprogramming cells from each of said populations of late-outgrowth EP cells into reprogrammed cells.

Suitable formats for high-throughput reprogramming are well known in the art. For example, the cells are reprogrammed in a multiwall tissue culture dish, for example a 96 well tissue culture dish, as described above.

A population of late-outgrowth EP cells may be a cultured late-outgrowth EP cell line which has been cultured or expanded from one or more late-outgrowth EP cells produced from a blood sample, as described above.

Cells from each population of late-outgrowth EP cells may be reprogrammed separately, for example in a separate well of a multiwell tissue culture dish. Late-outgrowth EP cells produced from samples obtained from different individuals may be reprogrammed simultaneously in separate vessels, for example separate wells of a multiwall tissue culture dish.

Conveniently, at least 1000, at least 2000, at least 3000, or at least 4000 cells from a population of late-outgrowth EP cells (i.e. late-outgrowth EP cell line) may be reprogrammed in a single vessel, such as a well of a multiwell tissue culture dish. One or more, two or more, or three or more reprogrammed cells may be produced in each well from these cells. Up to 10, up to 9, up to 8, up to 7 or up to 6 reprogrammed cells may be produced in each well, typically 3 to 6. Each individual reprogrammed cell may proliferate to produce a colony. Another aspect of the invention provides a reprogrammed mammalian cell produced by a method described above.

In some embodiments, reprogrammed cells produced as described herein from late outgrowth EP cells from a first cohort of individuals may be compared with reprogrammed cells produced as described herein from late outgrowth EP cells from a second cohort of individuals. For example, the properties and behaviour of reprogrammed cells, such as iPS cells, from different patient cohorts may be compared. This may be useful for example in disease modelling or drug screening.

Differences in the derivation conditions of iPSCs commonly lead to differences in the properties of resulting iPSCs. These differences can affect the differentiation potential or phenotypes of the cells derived from the iPSCs. The methods described herein limit these variations by allowing many patient cell-lines for a specific disease or groups of diseases to be derived simultaneously.

Another aspect of the invention provides a method of screening for a compound useful in the treatment of a disease comprising;
contacting isolated reprogrammed cell produced by a method described above with a test compound, and;
determining the effect of the test compound on said cells and/or the effect of said reprogrammed cells on the test compound.

Suitable reprogrammed cells are described above.

The reprogrammed cells may display a disease phenotype and the effect of the test compound on one or more disease pathologies in the reprogrammed cells may be determined. A decrease or amelioration of one or more disease pathologies in the reprogrammed cells in the presence, relative to the absence of test compound is indicative that the test compound may be useful in the treatment of the disease in the individual.

Suitable disease conditions and phenotypes are described above.

The reprogrammed cells may display a normal phenotype and the effect of the test compound on the growth, differentiation or viability of the reprogrammed cells or the ability of the reprogrammed cells to perform one or more cell functions may be determined. In some embodiments, cells may be modified to express reporters that can be used to measure particular cell functions or attributes. A decrease in growth, viability or ability to perform one or more cellular functions may be indicative that the compound has a cytotoxic effect (see for example, Barbaric I et al Biochem Soc Trans. 2010 August; 38(4):1046-50).

Various further aspects and embodiments of the present invention will be apparent to those skilled in the art in view of the present disclosure.

All documents mentioned in this specification, including sequence database entries, are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

EXAMPLES

Certain aspects and embodiments of the invention will now be illustrated by way of example and with reference to the figures described below.

FIG. 1 shows a summary of methodology and basic characterisation of EPC-iPSCs.

FIG. 1A shows an overview of EPC derivation leading into (i) iPSC derivation in standard 10 cm dishes and (ii) 96-well high-throughput method. Mononuclear cells (MNC) are isolated from non-mobilized peripheral blood by ficoll gradient centrifugation. These cells are cultured on collagen in endothelial growth medium and after ~7 days 'early' outgrowth EPCs emerge. These have a dendritic morphology and are distinct from 'late' outgrowth EPCs. Culture conditions are maintained and 'late' outgrowth EPCs emerge after ~10-14 days of laying down the original MNC culture. These cells have a cobble stone morphology characteristic of endothelial-type cells and express markers distinct from 'early' outgrowth EPCs.

Figure 1B:
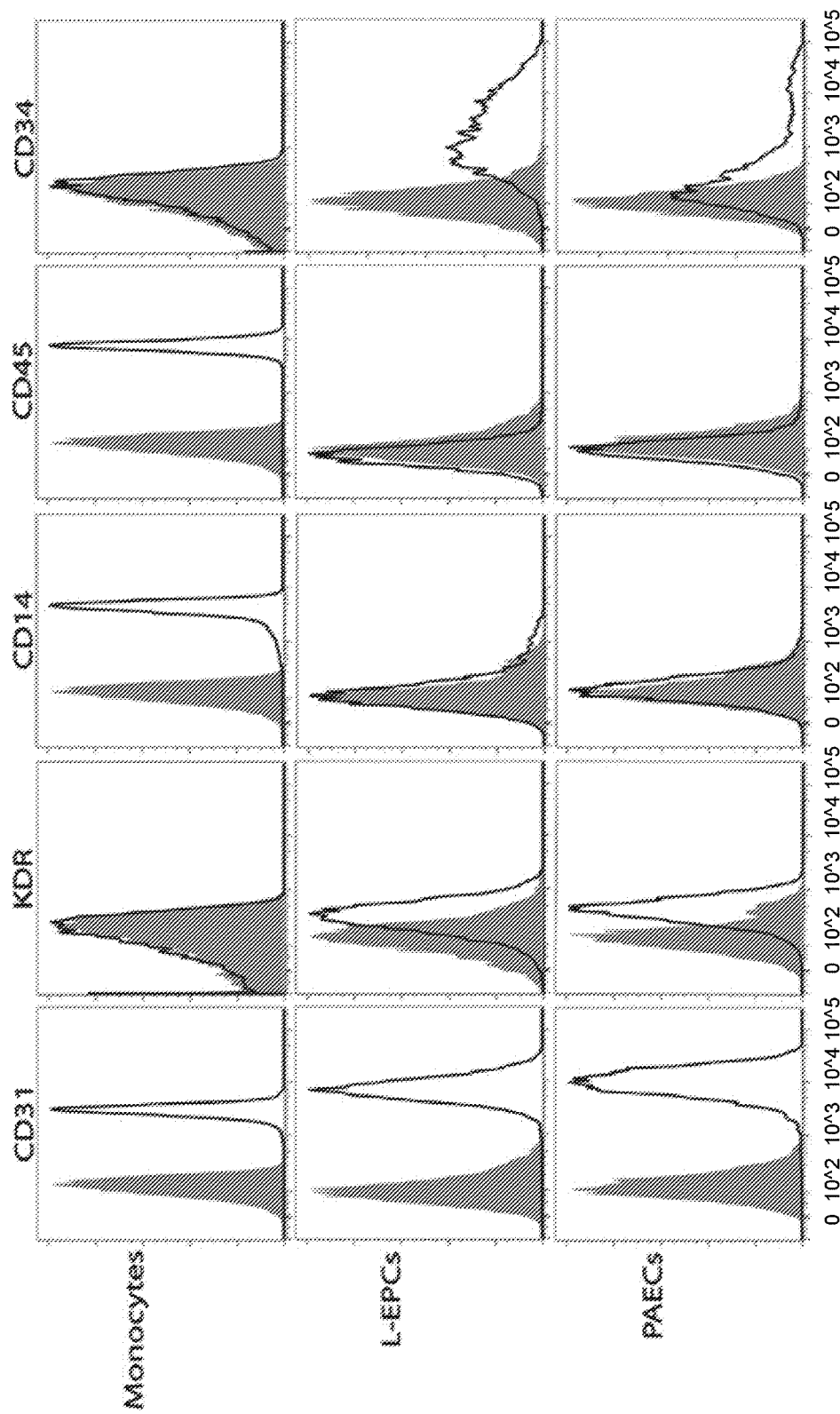

FIG. 1B shows flow cytometric analysis demonstrating similar surface marker expression in L-EPCs and pulmonary artery endothelial cells, when compared with freshly isolated monocytes.

Figure 1C:
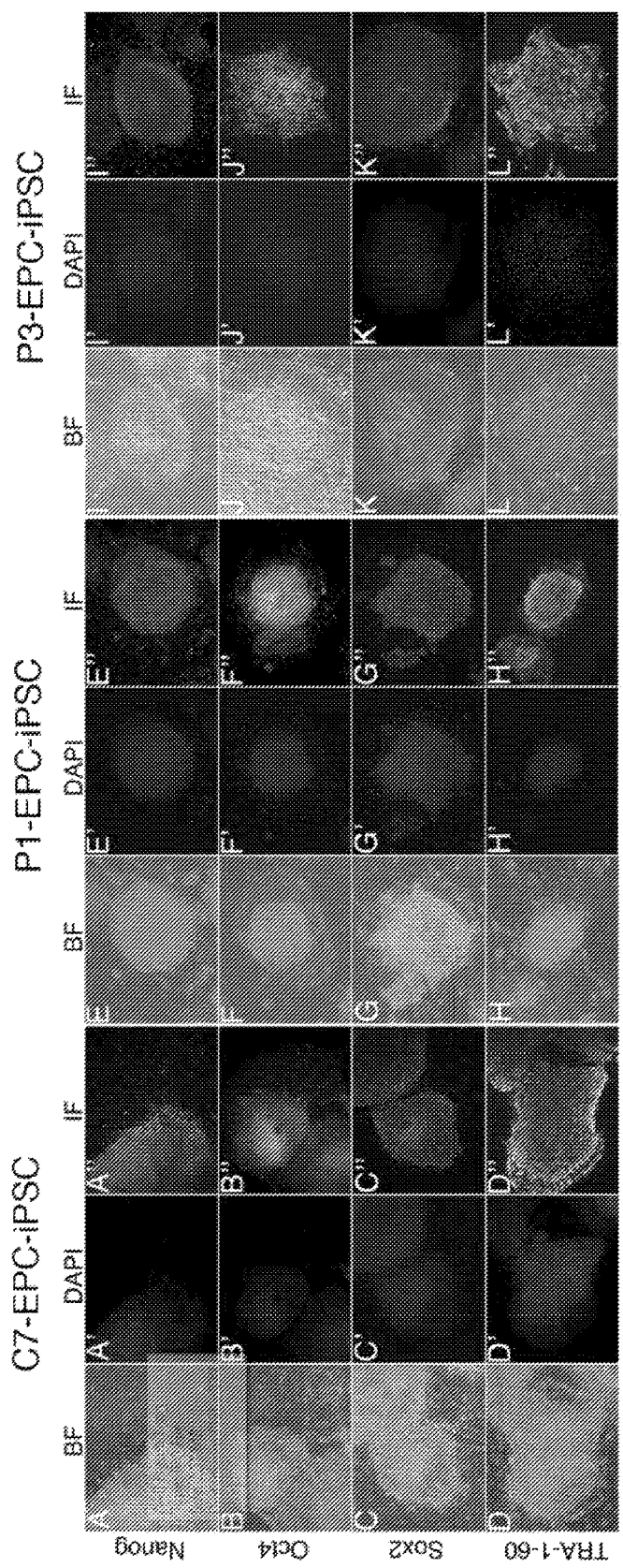

FIG. 1C shows pluripotency marker expression in 3 exemplar lines of iPSC generated from EPCs. Panel A, A', A"-D, D', D" EPC1 (from wild-type patient), Panel E, E', E"-H, H', HH" EPC2 (from a Bmpr2+/− patient presenting with PAH) and Panel I, I', I"-L, L', L" EPC4 (from a non-BMPR2 mutant idiopathic patient presenting with PAH) derived iPSC all express markers consistent with a pluripotent state.

Figure 2:
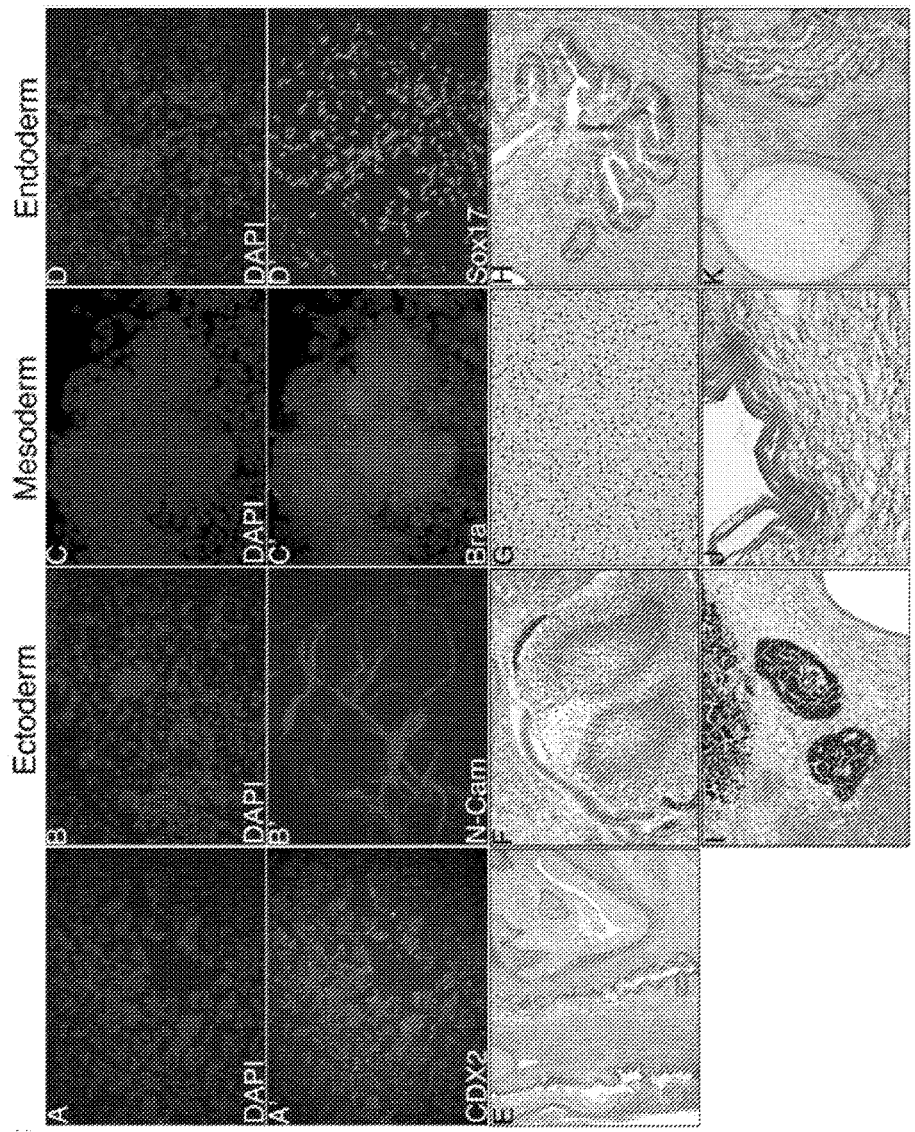
FIG. 2 shows in vitro and in vivo differentiation capacity of EPC-iPSC to form germ layers and germ layer derivatives.

FIG. 2 shows In vitro and in vivo differentiation capacity of EPC-iPSC to form germ layers and germ layer derivatives. Panels A-D show DAPI staining and panels A'-D' show immunostaining. Germ layer specific marker analysis of serum directed differentiated EPC-iPSCs in vitro revels EPC-iPSCs are capable of differentiation into ectoderm (N-Cam, B'), mesoderm (Bra, C') and endoderm (Sox17, D'). These cells can also differentiate into extra-embryonic ectoderm (CDX2, A'). Panels E to K show in vivo teratoma analysis of germ layer differentiation and demonstrates that ECP-iPSCs can differentiate into derivatives of all three germ layers (E and I, histological overviews of teratoma morphology showing derivatives of all three germ layers (notably striated epithelium (ectoderm), smooth muscle (mesoderm) and respiratory tracts (endoderm)) juxtaposed as is characteristic for teratomas derived from pluripotent cells: F neuroectoderm (ectoderm), G cartilage (mesoderm), H respiratory tracts (endoderm), I melanocytes (ectoderm), J connective tissue (mesoderm), K gastrointestinal tracts (endoderm)).

FIG. 3 shows that EPC have significantly higher kinetics and efficiency of reprogramming than fibroblasts.

Figure 3A:
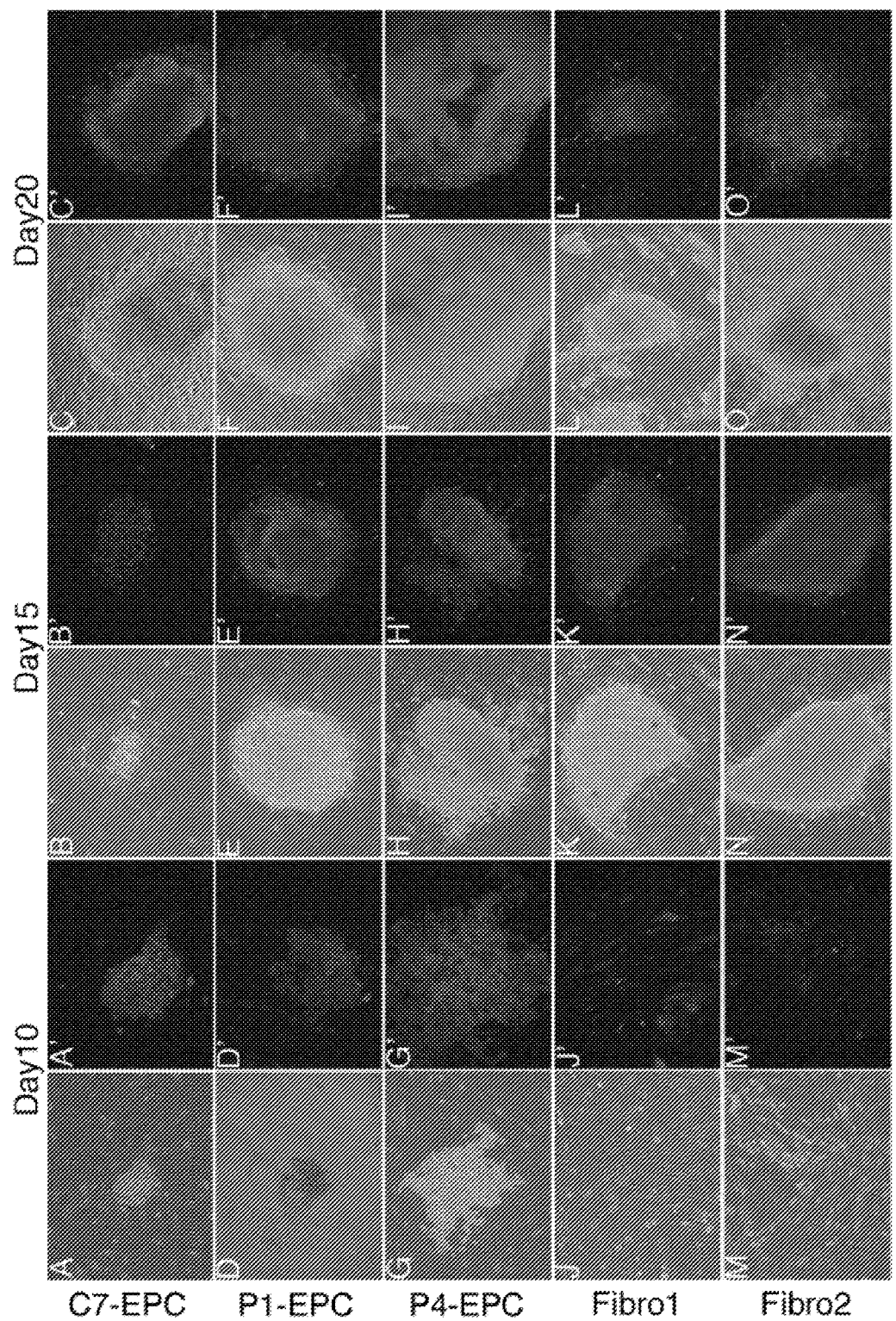
FIGS. 3A-3C shows that EPC have significantly higher kinetics and efficiency of reprogramming than fibroblasts.

FIG. 3A shows the kinetics of iPSC generation from EPCs compared with Fibroblasts. Panels A-O show bright field, and panels A'-O' show immunostaining for Nanog. Panels A/A', D/D', G/G', J/J', M/M' are at day 10 following commencement of reprogramming, panels B/B', E/E', H/H', K/K', N/N' are at day 15 following commencement of reprogramming, panels C/C', F/F', I/I', L/L', O/O' are at day 20 following commencement of reprogramming. Nanog positive iPSC-like colonies emerge 10 days after expression of nuclear reprogramming factors in EPCs (A/A'-I/I') compared with fibroblast, which emerge after 15 days (J/J'-O/O').

Figure 3B:
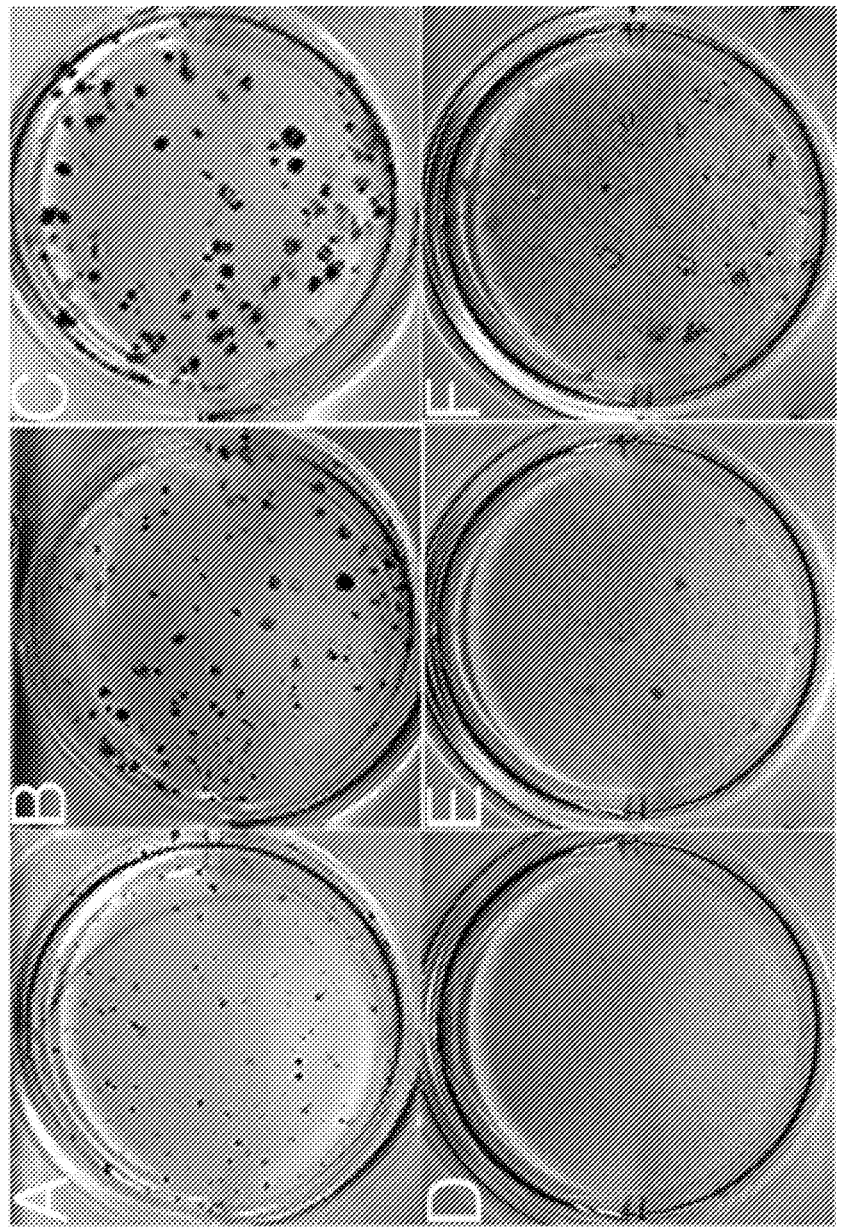

FIG. 3B shows a comparison of iPSC derivation efficiency between EPCs and Fibroblasts. Panels A-C show EPC1 cells and Panels D-F show a fibroblast cell line. Panels A and D show day 10 of reprogramming. Panels B and E show day 15 of reprogramming and Panels C and F show day 20 of reprogramming.

Figure 3C:
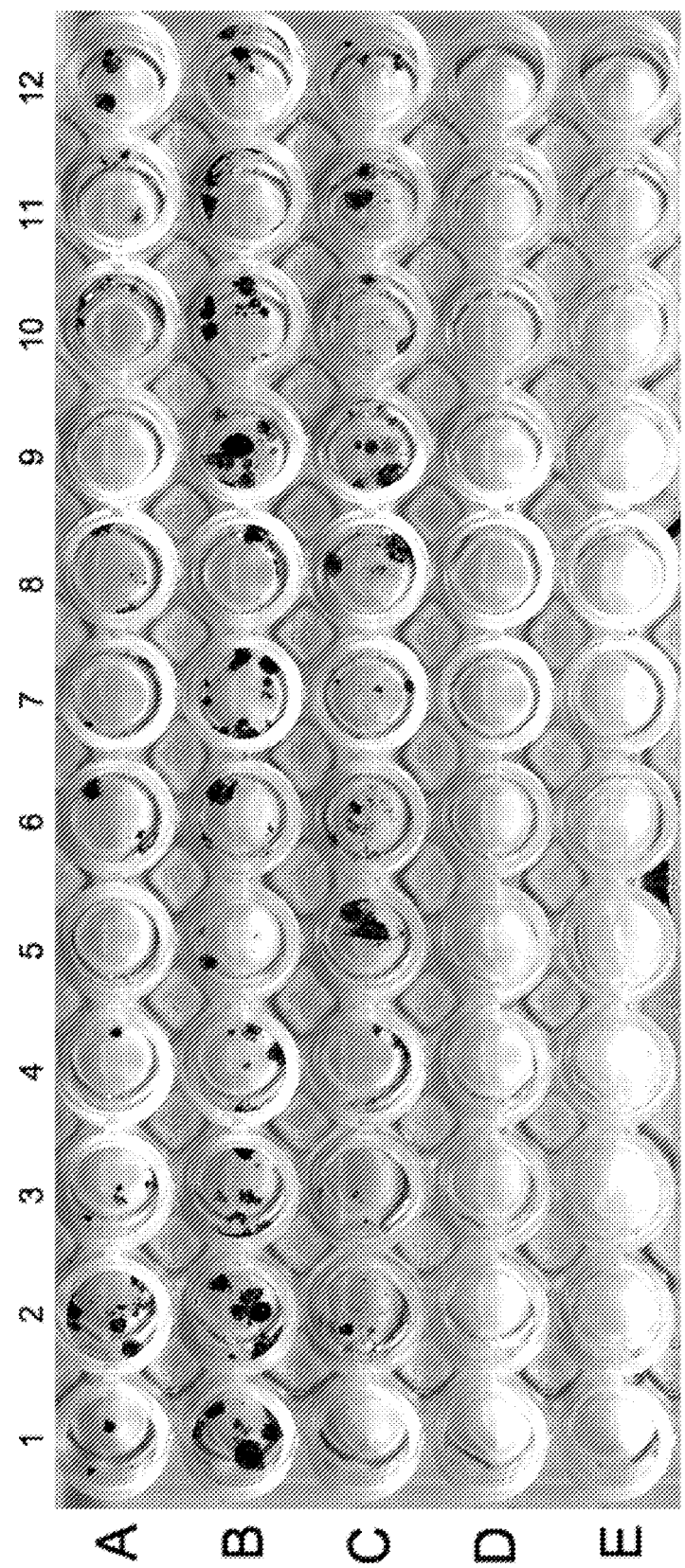

FIG. 3C shows high-throughput generation of iPSCs using EPCs and as cellular substrates in 96-well format. Alkaline phosphatase stained iPSC colonies appeared black. Row A EPC4-iPSC, Row B EPC-iPSC, Row C EPC-iPSC, Row D Fibroblast1-iPSC, Row E Fibroblast2-iPSC.

Figure 4:
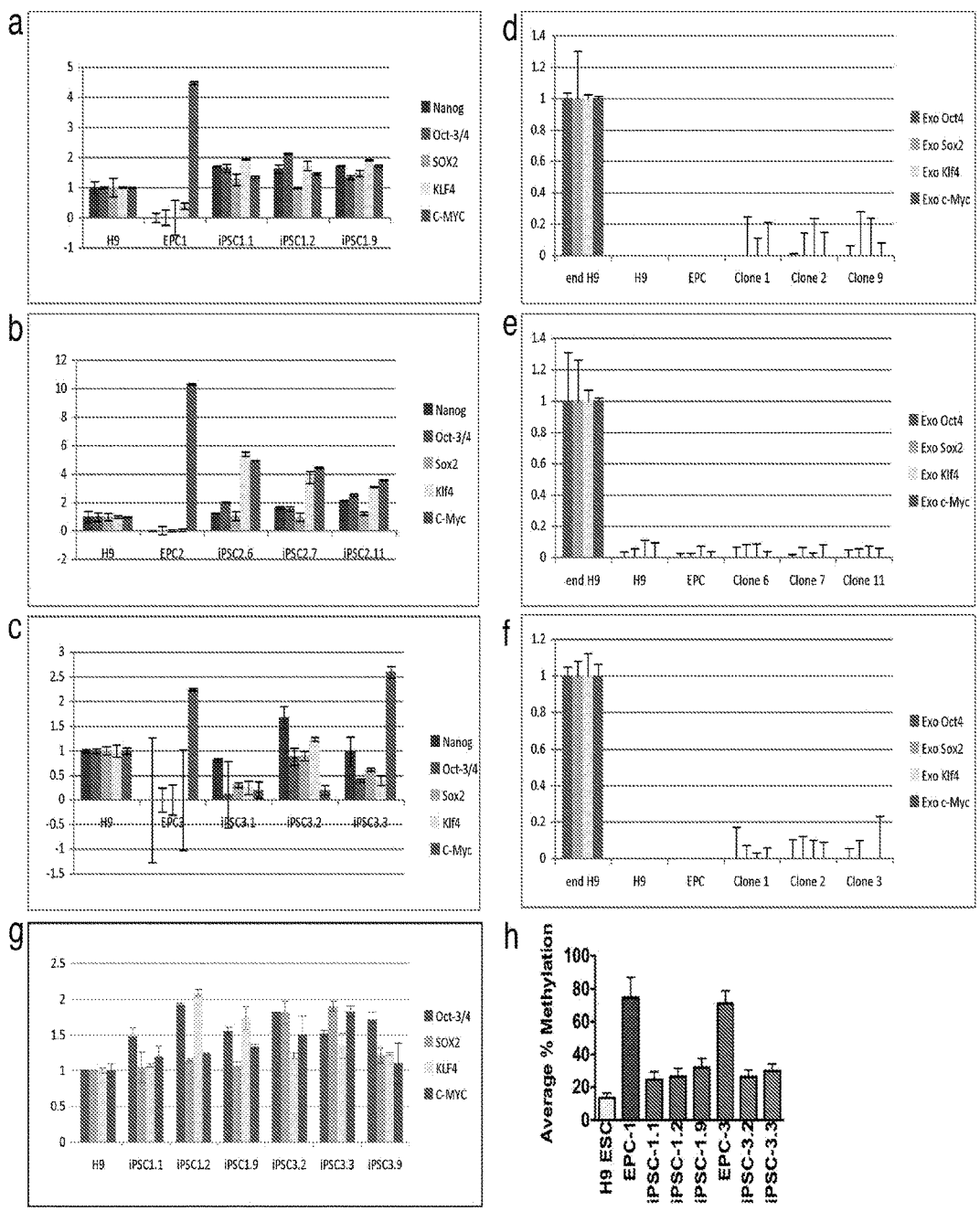
FIG. 4 shows viral integration copy number analysis.

FIG. 4 shows viral integration copy number analysis. FIGS. 4A-C, show endogenous expression of Nanog, Oct4, Sox2, Klf4 and c-Myc relative to the levels in H9 embryonic stem cell (ESC) line, Note that c-Myc appears to be expressed more highly in L-EPCs than the other reprogramming factors. FIGS. 4D-F show exogenous Oct4, Sox2, Klf4 and c-Myc expression from the reprogramming viral insertions. FIG. 4G shows viral insertion copy numbers in iPSCs relative to endogenous copy numbers of the four reprogramming factors in H9 ESCs. Insertion rates were calculated as previously published. FIG. 4H shows pyrosequencing of the Oct4 promoter in EPC-iPSCs revels that the methylation state of the Oct 4 promoter in EPC-iPSCs more closely resembles that of H9 hESCs, rather than the corresponding EPC parent lines.

Table 1 shows a table/graph of colony numbers on day 10, 15 and 20 using EPCs compared with fibroblasts.

Table 2 shows a table/graph of colony numbers using EPCs compared Fibroblasts in the 96 well format experiments.

Table 3 shows aCGH analysis of L-EPC genomes compared to matched monocyte genomes.

Table 4 shows aCGH analysis of EPC-iPSC genomes compared to parental L-EPC genomes.

Table 5 shows aCGH analysis of EPC-iPSC genomes compared to matched monocyte genomes.

Experiments

Methods

Isolation and Characterization of L-EPCs

Human mononuclear cells were obtained from 40 to 80 mL of peripheral blood by density gradient centrifugation using Ficoll Paque Plus (GE Healthcare). Washed samples were cultured at approximately $1.5 \times 10^6$ cells/cm$^2$ on collagen (BD Biosciences, Franklin Lakes, N.J.)-coated flasks in EGM-2MV medium (Lonza, Basel, Switzerland) containing 20% embryonic stem cell-grade fetal bovine serum (Hyclone, Thermo Scientific, Hampshire, UK). Culture media was changed every two days. Late-outgrowth EPCs appeared between 10 and 21 days in culture. Following generation, EPCs were passaged onto tissue culture plastic and maintained in EGM-2MV containing 10% standard FBS (Gibco, Invitrogen, Paisley, UK).

Flow Cytometry Methods

PBMNCs were isolated from whole blood samples by ficoll density gradient centrifugation and monocytes were isolated by positive magnetic selection using CD14-microbeads (Miltenyi Biotec, Bergisch Gladbach, Germany) as per manufacturer's instructions. L-EPCs and HPAECs were trypsinized prior to resuspension of all three cell types in staining buffer containing 2% FBS and 2 mM EDTA. Monocytes, EPCs and HPAECs were stained with APC-conjugated mouse-α-human VEGFR2 (clone 89106, R&D Systems, Minneapolis, Minn.), FITC-conjugated mouse-α-human CD31 (clone WM59), APC-conjugated mouse-α-human CD34 (clone 581), FITC-conjugated mouse-α-human CD14 (clone M5E2) and FITC-conjugated mouse-α-human CD45 (clone HI30, all from BD Biosciences, Franklin Lakes, N.J.) or the appropriate isotype controls.

Generation and Culturing of Fibro-iPSCs and L-EPC-iPSCs

Generation and culturing of Fibro-iPSC was performed as previously described (Vallier et al., 2009; Yusa et al (2011). Nature 478, 391-4) using 100,000 starting cells and with the following modifications. Fibroblasts were transduced at 32° C. The next day cells were washed 3 times with PBS and switched to MEF medium at 37° C., on day 5 cells were split and added to a MEF feeder plate. From day 7 cells were cultured in KSR+FGF2 medium. L-EPC-iPSC generation and culturing was performed essentially the same as for Fibro-iPSCs except that L-EPCs were maintained in EGM-2MV+10% serum until day 5 when they were transferred to MEF coated feeder plates and MEF medium. Percentage reprogramming efficiency was calculated thus: iPSC colony number at day 20/33,333×100.

Assessment of Oct4 Promoter Methylation, BS-PCR and Pyrosequencing

Bisulfite modification of genomic DNA (1 microgram) was performed using the EpiTect DNA methylation kit (Qiagen, Crawley, UK) as recommended by the manufacturer. Bisulfite-PCR was performed to amplify the promoter region of the Oct3/4 gene (GRCh37, Chr6: 31,140,564-31,140,784), using previously reported primers5. The reverse primer was biotinylated for the template strand and the Streptavidin captured single strand DNA was pyrosequenced using 'Pyrosequencing primers 2 and 3' to cover all the CpGs sites within this region with the exception of the first CpG. The first CpG was pyrosequenced using the Biotinylated Forward primer for the BS-PCR instead and pyrosequenced performed using the 'pyrosequencing primer-4'. Pyrosequencing runs were performed using Pyro-Gold Q96 SQA reagents on the PyroMark ID pyrosequencer (Qiagen, Crawley, UK) as per manufacturer's recommendation. The pyrosequencing data were analyzed using Pyro Q-CpG software (Qiagen, Crawley, UK) and results presented as percentage methylation for each of the CpG sites.

BS-PCR Conditions:

BS-PCR was performed at 3 mM final magnesium chloride concentration as follows: 95° C. 10 min; 50 cycles of 95° C. 20 sec, 55° C. 20 sec, 72° C. 1 min; and one cycle of 72° C. 10 min.

CGH Analysis

CGH analysis was performed and CNVs called as previously described (Yasu, et al., 2011). In summary, genomic DNA was extracted using DNeasy kit (Qiagen). Agilent 244k human genome arrays were used following manufacturer's protocol. The arrays were scanned using an Agilent microarray scanner and the data were generated by Agilent Feature Extraction software. The analysis was performed using Agilent Genomic Workbench software and CGH calls were made using ADM-2 algorithm (6.0 threshold) with a minimum of 3 consecutive probes detecting a region of abnormality.

Directed Differentiation in Chemically Defined Medium

Serum directed differentiation of extraembyonic and neuroectoderm were performed as previously described (Vallier et al., 2009). Mesendoderm differentiation we performed in a 3 day differentiation protocol in the following way; day1 cells were cultured in CDM+PVA (as previously described)+Activin 100 ng/ml+fgf2 100 ng/ml+bmp4 10 ng/ml+Ly 10 uM+chir 3 uM. On day2 cells were switched to Activin 100 ng/ml+fgf2 100 ng/ml+bmp4 10 ng/ml+Ly 10 uM excluding chir. On day3 cells were switched to RPMI medium+Activin 100 ng/ml+fgf2 100 ng/ml Generation of Teratomas EPC-iPSCs were injected into SCID or SCID Beige mice either intra-peritoneal, intra-muscular or under the kidney capsule. Mice were maintained for at least 14 weeks post injection of iPSCs and every care was taken in following strict local ethical policies and home office rules concerning animal uses and regulated procedures.

Immunostaining

Immunostaining was performed as previously described (Vallier et al., 2009), with donkey and goat serum C07SA from Serotec. A list of primary antibodies can be found in Supplementary Table 3

Alkaline Phosphatase Method

Cells were fixed in 4% PFA for 20 min at 4C, then rinsed 3 times in PBS followed by AP solution: Tris 0.1M pH 9.5 NaCl 0.1M. They were then incubated for 24 h at 4° C. in 10 ml AP solution supplemented with 200 ul of Nitro Blue Tetrazolium+20 ul BCIP (5-bromo-4-chloro-3indolyl-phosphatase) Promega cat #S3771. Finally cells were washed with PBS once staining was complete.

Viral Insertion Copy Number Analysis

Viral insertion copy number analysis was performed as previously described (Vallier et al., 2009) using Quant-iT DNA Assay Kit, Broad Range (Molecular Probes Q33135).

Results

EPCs were obtained from control subjects and from patients with the heritable form of pulmonary arterial hypertension, the majority (>70%) of which are due to mutations in the bone morphogenetic protein type II receptor (BMPR-II).

FIG. 1A provides an overview of the approach we used to generate iPSCs from EPCs. In brief, EPCs were isolated by sampling 40-80 mls of non-mobilized venous blood and performing a density gradient centrifugation to isolate cells of the mononuclear compartment. These cells were then plated in a tissue culture dish on collagen and maintained in growth medium enriched for endothelial cell survival. After 10 to 14 days, late outgrowth colonies of EPCs emerged from highly monocytic "early" EPC cultures (typically 2-7 colonies) and began to proliferate whilst remaining cells either senesced or were non-dividing.). In our hands L-EPCs were isolated from all individuals tested (n=20) using 40 mls of blood. L-EPCs were highly proliferative, doubling every 24-28 hrs, could be passaged (at least 10 times) and could be frozen and thawed without loss of viability. Importantly, we also found that EPCs are readily generated from frozen mononuclear cell preparations, which makes storage and transportation of samples straightforward. To confirm the robustness of L-EPCs as a cellular substrate we derived iPSCs using cells from healthy control subjects (n=3) and from patients with heritable pulmonary arterial hypertension (PAH), a condition characterised by endothelial dysfunction (n=5) (International PPH Consortium, et al. *Nat Genet.* 26(1):81-4 (2000)). These EPCs were then used for the generation of iPSCs.

As part of this study, we modified a standard EPC isolation protocol to include the use of embryonic stem cell grade fetal calf serum. Using this new protocol, we were consistently able to isolate EPCs from non-mobilized peripheral blood with a success rate of >90%. iPSC generation was performed by standard techniques using the exogenous expression of Oct4, Sox2, Klf4 and c-Myc (Takahashi et al 2006; Takahashi et al 2007; Seki et al 2010; Loh et al 2010; Staerk et al 2010), having first tested for the expression of these factors in EPCs and found them to be either not expressed or in the case of c-Myc expressed at extremely low levels. Given the expression of c-Myc in EPCs we attempted to reprogram EPCs using only Oct4, Sox2 and Klf4. This was unsuccessful suggesting that the endogenous levels of c-Myc expression in EPCs are inadequate to contribute to nuclear reprogramming. In these studies, L-EPCs were derived from three healthy control individuals (C4-EPC, C7-EPC and C8-EPC) and five samples from patients with PAH. Three patients carried a mutation in BMPR2 (P2-EPC and P3-EPC carried a W9X mutation, P5-EPC carried a C347Y mutation) (International PPH Consortium, et al., 2000). In two patients (P1-EPC and P4-EPC) no mutation was identified. As comparators of reprogramming dynamics we used fibroblast lines, CRL (Fibro1) and PatientB (Fibro2), previously shown to reprogramme to iPSCs at the higher end of fibroblast reprogramming efficiency (Vallier et al (2009)).

Following exogenous expression of the four reprogramming factors pluripotency marker expression confirmed that EPCs were reprogrammed to a state resembling human embryonic stem cells (hESC) (FIG. 1C and FIG. 4). These cells were karyotypically normal as judged by CGH analysis and importantly more stable than those iPSCs generated from fibroblasts, which when reprogrammed have been shown to lead to iPSC with increased CNVs and genomic aneuploidy. They also showed appropriate de-methylation of the Oct4 promoter and, where retroviruses were used, had the exogenous expression of the reprogramming factors, which inserted at 1-2 copies per factor, appropriately silenced (FIG. 4). The pluripotent potential of these cells was tested in in vitro differentiation assays. We confirmed expression of markers associated with each of the three germ layers, ectoderm, mesoderm and endoderm and extra-embryonic tissues (FIG. 2). We further tested whether reprogrammed EPCs could generate teratomas in vivo by injecting cells into immunocompromised mice. Analysis of the resulting tumours clearly demonstrated structures and cell types specific to each of the three germ layers, confirming the pluripotent nature of the reprogrammed EPCs and that the reprogrammed cells fulfilled the criteria for iPSCs (FIG. 2).

Notably we have been able to generate iPSCs from all EPC lines we tested including both control and patients, demonstrating that EPCs are obtainable from patients with severe vascular disease and can be reprogrammed to a pluripotent state. The ease with which the reprogramming substrate can be obtained from patients and controls is a major advantage of this method.

A critical step in the translation of iPSC technology for clinical and industrial applications for disease modelling and drug screening, is the derivation of iPSC lines in chemically defined media without feeder cell contamination. We have found that feeder-free iPSCs derive readily from EPCs for all lines tested (n=5), which is better than from skin fibroblasts in our hands. We have also observed that the EPC derived feeder-free iPSC are less prone to autonomous differentiation and are more likely to maintain their pluripotent state. This property of EPC-derived iPSCs will make differentiation assays more precise and controlled, which is highly desirable for disease modelling and drug screening and isolation of cells for transplantation. We further observed four striking features during EPC reprogramming relative to the reprogramming of fibroblasts. In these experiments, we used a fibroblast-derived iPSC lines previously shown to convert to iPSCs at the higher end of fibroblast reprogramming efficiency. Firstly, nanog and alkaline positive hESC/iPSC-like colonies appeared by 10 days after expression of the reprogramming factors, compared to 15 days for the control fibroblasts used, providing indication that the kinetics of EPC reprogramming was significantly faster (FIGS. 3A, 3B). Secondly, the hESC/iPSC-like colonies that formed from EPCs were larger and more robust than those obtained with fibroblasts, which enhanced our ability to pick these colonies and expand them (FIGS. 3A, 3B). Thirdly, the number of partially reprogrammed cells observed was significantly lower during the reprogramming of EPCs to iPSCs than the number that form during the reprogramming of fibroblasts to iPSCs. This provides an important technical advance as it becomes easier to pick iPSC colonies and sub-culture purer iPSC clones (FIG. 3B). Fourthly, iPSC colonies formed from L-EPCs with an average efficiency of 0.22%, around 10-fold more frequently than fibroblast-derived colonies (FIG. 3B-C).

We took advantage of these striking features of EPC reprogramming and designed a method that could be used to generate iPSCs from a limited number of cells in parallel. We added either 4000 EPCs or fibroblasts to single wells of a 96-well tissue culture dish, without feeders, and infected the cells with viruses expressing the four reprogramming factors (FIG. 3C). For each EPC or fibroblast line we set up 12 independent wells for comparison of efficiency. On day 5 post-infection, mouse embryonic fibroblast (MEF) feeder cells were added to each well, and the cells were allowed to adhere. By doing this we avoided stressing the EPCs and fibroblasts with a trypsinization step. The cells were then left for a further 10 days and stained for alkaline phosphatase activity (FIG. 3C). No iPSC colonies appeared in any of the 12 wells for either fibroblast cell line used. In contrast, 3-6 colonies were observed in 34/36 wells for the three L-EPC lines tested, with colonies observed in all twelve wells for two of the EPC lines and eleven of the twelve wells for the third (Table 2). This clearly demonstrates for the first time that human iPSCs may be isolated from multiple individuals in parallel. Given this high efficiency resulting in 3-6 colonies per well, 32-48 patient EPC lines may be processed per 96-well dish (2-3 wells per EPC line). This provides a potential 6-18 iPSC lines per patient EPC line for further analyses. This significantly reduces the costs involved in iPSC generation. Furthermore, an important caveat to using iPSCs in comparative analyses between patient cohorts is that differences in the exact conditions the iPSCs were generated can affect their differentiation potential and may potentially contribute to the differences observed in epigenomic and genomic characteristics in iPSCs at least during early passages. Using our method as many as 48 patients can be processed under the same conditions in the same dish at the same time.

These methods allow large scale comparative studies on the differentiation potential and behaviours of iPSCs, and their derivatives, between different patient cohorts, to be performed with higher confidence that our data are not being skewed due to differences in the differentiation potential/behaviours of the different iPSCs. This is of clear importance in disease modelling and drug screening, which are two of the major uses of iPSCs.

Given the apparent plastic trans-differentiation potential of L-EPCs together with our observations that EPCs can reprogram with relatively high efficiency, we tested whether fully differentiated ECs also had a greater capacity for nuclear reprogramming than fibroblasts. Our results demonstrated that L-EPCs have a 2-fold greater reprogramming efficiency than fibroblasts. This observation provides further evidence for the plastic nature of EPCs and EPC-like cells.

One potential source of copy number variations (CNVs) in iPSCs is the acquisition of abnormalities during somatic cell aging in vivo or prolonged culture ex vivo (Laurent, L. C. et al (2011). Cell Stem Cell 7, 106-18; Liang, Q, et al. (2008) PNAS U S A 11, 17453-6; The International Stem Cell Initiative, (2011) Nat. Biotechnology, doi:10.1038/nbt.2051). The karyotype of L-EPCs has been shown to be normal. To test the genomic stability of L-EPCs in culture, we performed array comparative genomic hybridization (aCGH) analysis at passage 3-4 (Table 3) compared to DNA from freshly isolated CD14+ monocytes from the same individual. This analysis revealed that the genomes of 5/6 L-EPC lines were either identical to their corresponding matched monocyte reference genome or demonstrated a single 13.1 kb copy gain at 1p21.3. This region contains the LCE3B/LCE3C genes, previously linked with susceptibility to psoriasis (de Cid (2009) Nat. Genet. 41, 211-5). Deletion of this region as assessed by aCGH occurs in 55-71% of European populations using whole blood derived DNA as the reference genome (de Cid (2009)), but is otherwise harmless. It is possible that the occurrence of independent copy gains of this specific region in 3/6 L-EPC genomes is explained by the common single copy loss of this region in the blood derived CD14+ monocytes, used as our reference genome. In one L-EPC line (C6-EPC, Table 3) a proportion [20-30%] of the L-EPC population appeared to have monosomy chromosome 18, although the majority of cells possessed a matched genome. Therefore, L-EPCs appear to demonstrate a reassuringly high level of genetic stability when compared with their parental cell of origin.

To determine the impact of reprogramming on copy number variation we conducted aCGH analysis on iPSCs grown for 3-11 passages compared with their corresponding parental EPC lines. Compared with parental L-EPC DNA, nine out of eleven EPC-iPSC lines (derived from 3 different EPC lines) showed no detectable genomic abnormalities (Table 4). The remaining two EPC-iPSC lines demonstrated single copy gains of regions of 36 or 632 kb compared with the corresponding parental L-EPC genome. These data demonstrate that it is possible to generate iPSCs whose genomes are unaltered compared with their parental cell type in a significant proportion of isolates. However, in comparison to fibroblasts, L-EPCs when established are clonal or oligoclonal, thus the normality of iPSCs derived from L-EPC lines may reflect the relatively close lineage history of the iPSCs and their progenitor cells, rather than unique properties of L-EPCs per se. Nevertheless, L-EPCs provide a potentially powerful tool for refining the reprogramming process for the production of genetically healthy iPSCs for clinical applications.

To examine this further, DNA from four EPC-iPSC lines from two subjects were compared with matched DNA derived from their CD14+ monocytes. One line from subject C7 showed a single copy gain and loss relative to its corresponding matched monocyte genome covering 230 kb. The three lines from individual C4 (at early passages, 3-4), showed between 10-17 copy number gains and losses compared to the matched monocyte genome (Table 5). The lack of consistency of the genomic analysis of L-EPCs versus iPSCs and iPSCs versus monocytes demonstrates the importance of the selected reference genome in reaching conclusions about the genome under assessment. The L-EPC vs iPSC comparisons were mostly normal because the EPCs are clonal, or nearly so, and the iPSCs were separated from their parental cells by relatively few cell divisions. The monocyte vs iPSC comparisons reflect the difference between clonal iPSCs and an average polyclonal somatic genome. Underlying somatic variation may make the derivation of "genetically pure" iPSCs impossible, since such a state might not exist in vivo (Laurent et al 20111; Liang et al 2008). Further studies will be necessary to define the natural occurrence of genomic changes in somatic cells and to understand the significance and consequences of these anomalies on derived iPSC lines. Clonal L-EPC lines could greatly facilitate these studies by simplifying the evaluation of the resulting variation in iPSCs by avoiding the use of potentially heterogeneous populations of somatic cells.

In conclusion, EPCs are readily obtainable from peripheral blood, with minimal manipulation. EPCs grow clonally, are highly proliferative, passageable and bankable and retain an unaltered genome in culture. Their use as nuclear reprogramming substrates will allow the routine and efficient high-throughput generation of personalized iPSCs in clinical and industrial settings for the first time. Importantly, they do not contain genome rearrangements akin to those seen in T-cells and cells carrying chromosomal rearrangements and are potentially available from patients with almost any disease or disorder, including vascular disease.

An important consideration to using iPSCs as a basis for cell based stem cell therapies, such as cell transplantation, is their genomic stability. The karyotype of EPC-iPSCs, as examined by CGH analysis, was found to be more stable than fibroblasts, which may perhaps also be reflected at the point mutation level. Importantly, late outgrowth EPCs reprogramme to iPSCs with high efficiency and are inherently more genomically stable during the reprogramming process. EPC-iPSCs have unaltered genomes compared to their late outgrowth EPC parent line.

Late outgrowth EPCs thus provide a significant new cellular model for the refinement of the reprogramming process to generate better iPSCs and other reprogrammed cells for cellular therapies. iPSCs produced from late outgrowth EPCs may also provide a very significant technology for drug and toxicology screens.

As proof-of-concept, we have successfully generated iPSCs from late outgrowth EPCs derived from control subjects and patients with the severe vascular disease, pulmonary arterial hypertension and shown to be karyotypically more stable than fibroblast derived iPSCs. These cells may be useful for target identification and drug discovery programmes. Recently, modified mRNAs have been used to generate iPSCs free from genomic integrations with high efficiencies (Warren et al 2010). The coupling of this technique with EPC reprogramming substrates, as described in this study, may be the final step in establishing a high-throughput, universally appropriate and standardised method of patient-personalised iPSC generation, resulting in cells that can be used safely in cellular transplantation therapies.

TABLE 1

| Cell Line | Number of iPSC colonies Day 10 | Number of iPSC colonies Day 15 | Number of iPSC colonies Day 20 | Percentage efficiency at 20 days | Fold efficiency normalized to the average of Fibro1 and Fibro2 |
|---|---|---|---|---|---|
| C7-EPC | 189 | 136 | 113 | 0.339% | 25.14 |
| P1-EPC | 10 | 15 | 67 | 0.201% | 9.57 |
| P3-EPC | 5 | 36 | 43 | 0.129% | 6.14 |
| Fibro1 | 0 | 2 | 9 | 0.027% | 1.29 |
| Fibro2 | 0 | 2 | 5 | 0.015% | 0.71 |

TABLE 2

| Cell line/row of 96-well dish | Column 1 | 2 | 3 | 4 | 5 | 6 | 7 | 8 | 9 | 10 | 11 | 12 | Average no. of colonies per well |
|---|---|---|---|---|---|---|---|---|---|---|---|---|---|
| P3-EPC/A | 2 | 7 | 4 | 2 | 0 | 2 | 3 | 4 | 2 | 4 | 4 | 2 | 3.0 |
| P1-EPC/B | 8 | 6 | 7 | 5 | 2 | 6 | 10 | 2 | 9 | 7 | 4 | 5 | 5.9 |
| C7-EPC/C | 0 | 2 | 2 | 2 | 3 | 4 | 4 | 2 | 8 | 5 | 2 | 3 | 3.1 |
| Control Fibroblast 1/D | 0 | 0 | 0 | 0 | 0 | 0 | 0 | 0 | 0 | 0 | 0 | 0 | 0 |
| Control Fibroblast 2/E | 0 | 0 | 0 | 0 | 0 | 0 | 0 | 0 | 0 | 0 | 0 | 0 | 0 |

TABLE 3

| Subject (C. healthy control) | Reference genome (from fresh blood sample) | EPC genome (passage 3-4) | Copy number variation | Chromosome and band | Size (kb) | Gene involved |
|---|---|---|---|---|---|---|
| C1 | C1 Monocyte | C1-EPC | None | | | |
| C2 | C2 Monocyte | C2-EPC | None | | | |
| C3 | C3 Monocyte | C3-EPC | 1 copy gain | 1q21.3 | 13.1 | LCE3C |
| C4 | C4 Monocyte | C4-EPC | 1 copy gain | 1q21.3 | 13.1 | LCE3C |
| C5 | C5 Monocyte | C5-EPC | 1 copy gain | 1q21.3 | 13.1 | LCE3C |
| C6 | C6 Monocyte | C6-EPC | Partial monosomy in 20-30% of population | Chromosome 18 | | |

TABLE 4

| Subject (P. patient with PAH) | Reference genome | EPC-iPSC line genome (Passages 3-9) | Copy number variation | Chromosome and band | Size (kb) | Genes |
|---|---|---|---|---|---|---|
| P1 | P1-EPC | P1-EPC-iPSC 1 | None | | | |
| | P1-EPC | P1-EPC-iPSC 2 | None | | | |
| | P1-EPC | P1-EPC-iPSC 3 | 1 copy gain | 15q14 | 36.6 | LOC723972 |
| P2 | P2-EPC | P2-EPC-iPSC 1 | None | | | |
| | P2-EPC | P2-EPC-iPSC 2 | None | | | |
| | P2-EPC | P2-EPC-iPSC 3 | None | | | |
| | P2-EPC | P2-EPC-iPSC 4 | 1 copy gain | 16q23.1 | 632.7 | NUDT7, VAT1L, CLEC3A, WWOX |
| | P2-EPC | P2-EPC-iPSC 5 | None | | | |
| P3 | P3-EPC | P3-EPC-iPSC 1 | None | | | |
| | P3-EPC | P3-EPC-iPSC 2 | None | | | |
| | P3-EPC | P3-EPC-iPSC 3 | None | | | |

TABLE 5

| Subject (C. healthy control) | Reference genome | EPC-iPSC line genome (Passages 3-9) | Copy number variation | Total DNA gain (kb) | Total DNA loss (kb) | Number of genes |
|---|---|---|---|---|---|---|
| C4 | C4-Monocyte | C4-EPC-iPSC 1 | 3 single copy gains, 11 single copy losses | 432.1 | 273.8 | 62 |
| | C4-Monocyte | C4-EPC-iPSC 2 | 2 single copy gains, 15 single copy losses | 173.4 | 592.8 | 70 |

TABLE 5-continued

| Subject (C. healthy control) | Reference genome | EPC-iPSC line genome (Passages 3-9) | Copy number variation | Total DNA gain (kb) | Total DNA loss (kb) | Number of genes |
|---|---|---|---|---|---|---|
| | C4-Monocyte | C4-EPC-iPSC 3 | 10 single copy losses | | 267.8 | 37 |
| C7 | C7-Monocyte | C7-EPC-iPSC 1 | 1 copy gain<br>1 copy loss | 143.2 | 91.9 | 3 |

The invention claimed is:

1. A method of producing human induced pluripotent stem (iPS) cells comprising:
   (i) providing an isolated population of human late-outgrowth endothelial progenitor (EP) cells,
   (ii) expressing Oct4, Sox2, Klf4 and c-Myc in said isolated population of human late-outgrowth EP cells; and
   (iii) culturing cells expressing Oct4, Sox2, Klf4 and c-Myc in a chemically defined embryonic stem (ES) cell medium to produce human iPS cells,
   wherein said isolated population of late-outgrowth human EP cells produces at least 2 fold more human iPS cells than an isolated population of human fibroblasts under identical conditions.

2. The method according to claim 1 comprising producing said isolated population of human late-outgrowth EP cells from a sample of blood obtained from an individual.

3. The method according to claim 2 further comprising obtaining said sample of blood from said individual.

4. The method according to claim 2 wherein the human late-outgrowth EP cells are produced by a method which comprises:
   (i) isolating mononuclear cell fraction from the sample of blood, and
   (ii) culturing mononuclear cells from the mononuclear cell fraction in endothelial cell culture medium for at least 8 days.

5. The method according to claim 2 wherein the individual has a disease condition.

6. The method according to claim 1 wherein the human iPS cells are isolated and/or purified following said culturing.

7. The method according to claim 1 further comprising providing said human late-outgrowth EP cells from two or more independent late-outgrowth EP cell lines.

8. The method according to claim 7 wherein said two or more late-outgrowth EP cell lines are produced from samples obtained from different individuals.

9. The method according to claim 7 comprising:
   (i) providing a plurality of samples of blood obtained from a population of individuals,
   (ii) producing a mixed population of late-outgrowth EP cells from each of said plurality of samples, and
   (ii) simultaneously reprogramming cells from each of said populations of late-outgrowth EP cells into human iPS cells.

10. The method of claim 1 wherein said isolated population of late-outgrowth EP cells are reprogrammed into human iPS cells at least 2 days before the isolated population of human fibroblasts under identical conditions.

* * * * *